(12) United States Patent
Devellian et al.

(10) Patent No.: US 7,871,419 B2
(45) Date of Patent: Jan. 18, 2011

(54) DELIVERY/RECOVERY SYSTEM FOR SEPTAL OCCLUDER

(75) Inventors: Carol A. Devellian, Topsfield, MA (US); David Widomski, Wakefield, MA (US); Andrzej J. Chanduszko, Chandler, AZ (US)

(73) Assignee: NMT Medical, Inc., Boston, MA (US)

( * ) Notice: Subject to any disclaimer, the term of this patent is extended or adjusted under 35 U.S.C. 154(b) by 298 days.

(21) Appl. No.: 11/070,027

(22) Filed: Mar. 2, 2005

(65) Prior Publication Data

US 2005/0267523 A1 Dec. 1, 2005

Related U.S. Application Data

(60) Provisional application No. 60/549,741, filed on Mar. 3, 2004, provisional application No. 60/569,422, filed on May 7, 2004.

(51) Int. Cl.
*A61B 17/08* (2006.01)
(52) U.S. Cl. .................................... 606/157; 606/213
(58) Field of Classification Search .............. 623/23.72; 606/213, 157; 604/104–109, 164.1, 164.11, 604/192, 540–544
See application file for complete search history.

(56) References Cited

U.S. PATENT DOCUMENTS

| | | |
|---|---|---|
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi, Jr. |
| 4,006,747 A | 2/1977 | Kronenthal et al. |
| 4,007,743 A | 2/1977 | Blake |
| 4,425,908 A | 1/1984 | Simon |
| 4,610,674 A | 9/1986 | Suzuki et al. |
| 4,626,245 A | 12/1986 | Weinstein |
| 4,696,300 A | 9/1987 | Anderson |
| 4,710,192 A | 12/1987 | Liotta et al. |

(Continued)

FOREIGN PATENT DOCUMENTS

EP 0 362 113 4/1990

(Continued)

OTHER PUBLICATIONS

International Search Report, International Application No. PCT/US03/17390, mailed on Oct. 6, 2003, 4 pgs.

(Continued)

*Primary Examiner*—Anhtuan T Nguyen
*Assistant Examiner*—Ryan J Severson
(74) *Attorney, Agent, or Firm*—Helen S. Liu

(57) ABSTRACT

A delivery/recovery system to allow an operator to deploy and recover a medical implant, such as an occluder for closing a patent foramen ovale (PFO). In one embodiment, the system includes a delivery mandrel for preventing the occluder from moving in the proximal direction, a delivery wire for securing the occluder to the delivery mandrel and preventing unwanted movement in the distal direction, and a sheath for enveloping the delivery wire, mandrel and occluder. By moving the sheath relative to the occluder in a series of steps, the occluder opens first on a distal side and then on a proximal side, in a manner that holds the occluder in place.

15 Claims, 23 Drawing Sheets

U.S. PATENT DOCUMENTS

| | | | |
|---|---|---|---|
| 4,836,204 A | 6/1989 | Landymore et al. | |
| 4,840,623 A | 6/1989 | Quackenbush | |
| 4,902,508 A | 2/1990 | Badylak et al. | |
| 4,915,107 A | 4/1990 | Rebuffat et al. | |
| 4,917,089 A | 4/1990 | Sideris | |
| 4,956,178 A | 9/1990 | Badylak et al. | |
| 5,021,059 A | 6/1991 | Kensey et al. | |
| 5,037,433 A | 8/1991 | Wilk et al. | |
| 5,041,129 A | 8/1991 | Hayhurst et al. | |
| 5,078,736 A | 1/1992 | Behl | |
| 5,106,913 A | 4/1992 | Yamaguchi et al. | |
| 5,108,420 A | 4/1992 | Marks | |
| 5,149,327 A | 9/1992 | Oshiyama | |
| 5,167,363 A | 12/1992 | Adkinson et al. | |
| 5,167,637 A | 12/1992 | Okada et al. | |
| 5,171,259 A | 12/1992 | Inoue | |
| 5,192,301 A | 3/1993 | Kamiya et al. | |
| 5,222,974 A | 6/1993 | Kensey et al. | |
| 5,226,879 A | 7/1993 | Ensminger et al. | |
| 5,236,440 A | 8/1993 | Hlavacek | |
| 5,245,023 A | 9/1993 | Peoples et al. | |
| 5,245,080 A | 9/1993 | Aubard et al. | |
| 5,257,637 A | 11/1993 | El Gazayerli | |
| 5,275,826 A | 1/1994 | Badylak et al. | |
| 5,282,827 A | 2/1994 | Kensey et al. | |
| 5,284,488 A | 2/1994 | Sideris | |
| 5,304,184 A | 4/1994 | Hathaway et al. | |
| 5,312,341 A | 5/1994 | Turi | |
| 5,312,435 A | 5/1994 | Nash et al. | |
| 5,316,262 A | 5/1994 | Koebler | |
| 5,334,217 A | 8/1994 | Das | |
| 5,350,363 A | 9/1994 | Goode et al. | |
| 5,354,308 A | 10/1994 | Simon et al. | |
| 5,411,481 A | 5/1995 | Allen et al. | |
| 5,413,584 A | 5/1995 | Schulze | |
| 5,417,699 A | 5/1995 | Klein et al. | |
| 5,425,744 A | 6/1995 | Fagan et al. | |
| 5,433,727 A | 7/1995 | Sideris | |
| 5,451,235 A | 9/1995 | Lock et al. | |
| 5,478,353 A | 12/1995 | Yoon | |
| 5,480,353 A | 1/1996 | Garza, Jr. | |
| 5,480,424 A | 1/1996 | Cox | |
| 5,486,193 A | 1/1996 | Bourne et al. | |
| 5,507,811 A | 4/1996 | Koike et al. | |
| 5,522,788 A | 6/1996 | Kuzmak | |
| 5,540,712 A | 7/1996 | Kleshinski et al. | |
| 5,562,632 A | 10/1996 | Davila et al. | |
| 5,577,299 A | 11/1996 | Thompson et al. | |
| 5,601,571 A | 2/1997 | Moss | |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,936 A | 6/1997 | Linden et al. | |
| 5,649,950 A | 7/1997 | Bourne et al. | |
| 5,649,959 A | 7/1997 | Hannam et al. | |
| 5,663,063 A | 9/1997 | Peoples et al. | |
| 5,683,411 A | 11/1997 | Kavteladze et al. | |
| 5,690,674 A | 11/1997 | Diaz | |
| 5,693,085 A | 12/1997 | Buirge et al. | |
| 5,702,421 A | 12/1997 | Schneidt | |
| 5,709,707 A | 1/1998 | Lock et al. | |
| 5,717,259 A | 2/1998 | Schexnayder | |
| 5,720,754 A | 2/1998 | Middleman et al. | |
| 5,725,552 A | 3/1998 | Kotula et al. | |
| 5,733,294 A | 3/1998 | Forber et al. | |
| 5,733,337 A | 3/1998 | Carr, Jr. et al. | |
| 5,741,297 A | 4/1998 | Simon | |
| 5,776,162 A | 7/1998 | Kleshinski | |
| 5,776,183 A | 7/1998 | Kanesaka et al. | |
| 5,797,960 A | 8/1998 | Stevens et al. | |
| 5,800,516 A | 9/1998 | Fine et al. | |
| 5,810,884 A | 9/1998 | Kim | |
| 5,823,956 A | 10/1998 | Roth et al. | |
| 5,829,447 A | 11/1998 | Stevens et al. | |
| 5,853,420 A | 12/1998 | Chevillon et al. | |
| 5,853,422 A * | 12/1998 | Huebsch et al. | 606/213 |
| 5,855,614 A | 1/1999 | Stevens et al. | |
| 5,861,003 A | 1/1999 | Latson et al. | |
| 5,865,791 A | 2/1999 | Whayne et al. | |
| 5,879,366 A | 3/1999 | Shaw et al. | |
| 5,893,856 A | 4/1999 | Jacob et al. | |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | |
| 5,928,250 A | 7/1999 | Koike et al. | |
| 5,944,738 A | 8/1999 | Amplatz et al. | |
| 5,955,110 A | 9/1999 | Patel et al. | |
| 5,976,174 A | 11/1999 | Ruiz | |
| 5,989,268 A | 11/1999 | Pugsley, Jr. et al. | |
| 5,993,475 A | 11/1999 | Lin et al. | |
| 5,993,844 A | 11/1999 | Abraham et al. | |
| 5,997,575 A | 12/1999 | Whitson et al. | |
| 6,010,517 A | 1/2000 | Baccaro | |
| 6,024,756 A | 2/2000 | Huebsch et al. | |
| 6,027,509 A | 2/2000 | Schatz et al. | |
| 6,030,007 A | 2/2000 | Bassily et al. | |
| 6,056,760 A | 5/2000 | Koike et al. | |
| 6,071,998 A | 6/2000 | Muller et al. | |
| 6,077,291 A | 6/2000 | Das | |
| 6,077,880 A | 6/2000 | Castillo et al. | |
| 6,079,414 A | 6/2000 | Roth | |
| 6,080,182 A | 6/2000 | Shaw et al. | |
| 6,096,347 A | 8/2000 | Geddes et al. | |
| 6,106,913 A | 8/2000 | Scardino et al. | |
| 6,113,609 A | 9/2000 | Adams | |
| 6,117,159 A | 9/2000 | Huebsch et al. | |
| 6,126,686 A | 10/2000 | Badylak et al. | |
| 6,132,438 A | 10/2000 | Fleischman et al. | |
| 6,143,037 A | 11/2000 | Goldstein et al. | |
| 6,152,144 A | 11/2000 | Lesh et al. | |
| 6,165,183 A | 12/2000 | Kuehn et al. | |
| 6,165,204 A | 12/2000 | Levinson et al. | |
| 6,171,329 B1 | 1/2001 | Shaw et al. | |
| 6,174,322 B1 | 1/2001 | Schneidt | |
| 6,174,330 B1 | 1/2001 | Stinson | |
| 6,187,039 B1 | 2/2001 | Hiles et al. | |
| 6,190,353 B1 | 2/2001 | Garibotto et al. | |
| 6,197,016 B1 | 3/2001 | Fourkas et al. | |
| 6,199,262 B1 | 3/2001 | Martin | |
| 6,206,895 B1 | 3/2001 | Levinson | |
| 6,206,907 B1 | 3/2001 | Marino et al. | |
| 6,214,029 B1 | 4/2001 | Thill et al. | |
| 6,217,590 B1 | 4/2001 | Levinson | |
| 6,221,092 B1 | 4/2001 | Koike et al. | |
| 6,227,139 B1 | 5/2001 | Nguyen et al. | |
| 6,228,097 B1 | 5/2001 | Levinson et al. | |
| 6,231,561 B1 | 5/2001 | Frazier et al. | |
| 6,245,080 B1 | 6/2001 | Levinson | |
| 6,245,537 B1 | 6/2001 | Williams et al. | |
| 6,261,309 B1 | 7/2001 | Urbanski | |
| 6,265,333 B1 | 7/2001 | Dzenis et al. | |
| 6,270,515 B1 | 8/2001 | Linden et al. | |
| 6,277,138 B1 | 8/2001 | Levinson et al. | |
| 6,277,139 B1 | 8/2001 | Levinson et al. | |
| 6,287,317 B1 | 9/2001 | Makower et al. | |
| 6,290,674 B1 | 9/2001 | Roue et al. | |
| 6,299,636 B1 | 10/2001 | Frantzen | |
| 6,306,150 B1 | 10/2001 | Levinson | |
| 6,306,424 B1 | 10/2001 | Vyakarnam et al. | |
| 6,312,443 B1 | 11/2001 | Stone | |
| 6,312,446 B1 | 11/2001 | Huebsch et al. | |
| 6,315,791 B1 | 11/2001 | Gingras et al. | |
| 6,316,262 B1 | 11/2001 | Huisman et al. | |

| | | | | | |
|---|---|---|---|---|---|
| 6,319,263 B1 | 11/2001 | Levinson | 2002/0022859 A1 | 2/2002 | Hogendijk |
| 6,322,548 B1 | 11/2001 | Payne et al. | 2002/0022860 A1 | 2/2002 | Borillo et al. |
| 6,328,727 B1 | 12/2001 | Frazier et al. | 2002/0026208 A1* | 2/2002 | Roe et al. ............... 606/190 |
| 6,334,872 B1 | 1/2002 | Termin et al. | 2002/0029048 A1 | 3/2002 | Miller |
| 6,342,064 B1 | 1/2002 | Koike et al. | 2002/0032459 A1 | 3/2002 | Horzewski et al. |
| 6,344,048 B1 | 2/2002 | Chin et al. | 2002/0032462 A1 | 3/2002 | Houser et al. |
| 6,344,049 B1 | 2/2002 | Levinson et al. | 2002/0034259 A1 | 3/2002 | Tada |
| 6,346,074 B1 | 2/2002 | Roth | 2002/0035374 A1 | 3/2002 | Borillo et al. |
| 6,348,041 B1 | 2/2002 | Klint | 2002/0043307 A1 | 4/2002 | Ishida et al. |
| 6,352,552 B1 | 3/2002 | Levinson et al. | 2002/0049457 A1 | 4/2002 | Kaplan et al. |
| 6,355,052 B1 | 3/2002 | Neuss et al. | 2002/0052572 A1 | 5/2002 | Franco et al. |
| 6,356,782 B1 | 3/2002 | Sirimanne et al. | 2002/0058989 A1 | 5/2002 | Chen et al. |
| 6,358,238 B1 | 3/2002 | Sherry | 2002/0077555 A1 | 6/2002 | Schwartz |
| 6,364,853 B1 | 4/2002 | French et al. | 2002/0095174 A1 | 7/2002 | Tsugita et al. |
| 6,371,904 B1 | 4/2002 | Sirimanne et al. | 2002/0096183 A1 | 7/2002 | Stevens et al. |
| 6,375,625 B1 | 4/2002 | French et al. | 2002/0099389 A1 | 7/2002 | Michler et al. |
| 6,375,671 B1 | 4/2002 | Kobayashi et al. | 2002/0099390 A1 | 7/2002 | Kaplan et al. |
| 6,379,342 B1 | 4/2002 | Levinson | 2002/0103492 A1 | 8/2002 | Kaplan et al. |
| 6,379,368 B1 | 4/2002 | Corcoran et al. | 2002/0107531 A1 | 8/2002 | Schreck et al. |
| 6,387,104 B1 | 5/2002 | Pugsley, Jr. et al. | 2002/0111537 A1 | 8/2002 | Taylor et al. |
| 6,398,796 B2 | 6/2002 | Levinson | 2002/0111637 A1 | 8/2002 | Kaplan et al. |
| 6,402,772 B1 | 6/2002 | Amplatz et al. | 2002/0111647 A1 | 8/2002 | Khairkhahan et al. |
| 6,419,669 B1 | 7/2002 | Frazier et al. | 2002/0120323 A1 | 8/2002 | Thompson et al. |
| 6,426,145 B1 | 7/2002 | Moroni | 2002/0128680 A1 | 9/2002 | Pavlovic |
| 6,436,088 B2 | 8/2002 | Frazier et al. | 2002/0129819 A1 | 9/2002 | Feldman et al. |
| 6,440,152 B1 | 8/2002 | Gainor et al. | 2002/0164729 A1 | 11/2002 | Skraly et al. |
| 6,450,987 B1 | 9/2002 | Kramer | 2002/0169377 A1 | 11/2002 | Khairkhahan et al. |
| 6,460,749 B1 | 10/2002 | Levinson et al. | 2002/0183786 A1 | 12/2002 | Girton |
| 6,482,224 B1 | 11/2002 | Michler et al. | 2002/0183787 A1* | 12/2002 | Wahr et al. ............... 606/213 |
| 6,488,706 B1 | 12/2002 | Solymar | 2002/0183823 A1 | 12/2002 | Pappu |
| 6,494,888 B1 | 12/2002 | Laufer et al. | 2002/0198563 A1 | 12/2002 | Gainor et al. |
| 6,508,828 B1 | 1/2003 | Akerfeldt et al. | 2003/0004533 A1 | 1/2003 | Dieck et al. |
| 6,514,515 B1 | 2/2003 | Williams | 2003/0023266 A1 | 1/2003 | Welch et al. |
| 6,548,569 B1 | 4/2003 | Williams et al. | 2003/0028213 A1 | 2/2003 | Thill et al. |
| 6,551,303 B1 | 4/2003 | Van Tassel et al. | 2003/0045893 A1 | 3/2003 | Ginn |
| 6,551,344 B2 | 4/2003 | Thill | 2003/0050665 A1 | 3/2003 | Ginn |
| 6,554,842 B2 | 4/2003 | Heuser et al. | 2003/0055455 A1 | 3/2003 | Yang et al. |
| 6,585,755 B2 | 7/2003 | Jackson et al. | 2003/0057156 A1 | 3/2003 | Peterson et al. |
| 6,596,013 B2 | 7/2003 | Yang et al. | 2003/0059640 A1 | 3/2003 | Marton et al. |
| 6,599,448 B1 | 7/2003 | Ehrhard, Jr. et al. | 2003/0065379 A1 | 4/2003 | Babbs et al. |
| 6,610,764 B1 | 8/2003 | Martin et al. | 2003/0100920 A1 | 5/2003 | Akin et al. |
| 6,623,508 B2 | 9/2003 | Shaw et al. | 2003/0120337 A1 | 6/2003 | Van Tassel et al. |
| 6,623,518 B2 | 9/2003 | Thompson et al. | 2003/0139819 A1 | 7/2003 | Beer et al. |
| 6,626,936 B2 | 9/2003 | Stinson | 2003/0171774 A1 | 9/2003 | Seigner et al. |
| 6,629,901 B2 | 10/2003 | Huang | 2003/0191495 A1 | 10/2003 | Ryan et al. |
| 6,666,861 B1 | 12/2003 | Grabek | 2003/0195530 A1 | 10/2003 | Thill |
| 6,669,722 B2 | 12/2003 | Chen et al. | 2003/0204203 A1 | 10/2003 | Khairkhahan et al. |
| 6,689,589 B2 | 2/2004 | Huisman et al. | 2004/0044361 A1 | 3/2004 | Frazier et al. |
| 6,712,804 B2 | 3/2004 | Roue et al. | 2004/0073242 A1 | 4/2004 | Chanduszko |
| 6,712,836 B1 | 3/2004 | Berg et al. | 2004/0087968 A1 | 5/2004 | Core |
| 6,726,696 B1 | 4/2004 | Houser et al. | 2004/0158124 A1 | 8/2004 | Okada |
| 6,790,173 B2 | 9/2004 | Saadat et al. | 2004/0176799 A1 | 9/2004 | Chanduszko et al. |
| 6,828,357 B1 | 12/2004 | Martin et al. | 2004/0210301 A1 | 10/2004 | Obermiller |
| 6,838,493 B2 | 1/2005 | Williams et al. | 2004/0234567 A1 | 11/2004 | Dawson |
| 6,867,247 B2 | 3/2005 | Williams et al. | 2004/0249367 A1 | 12/2004 | Saadat et al. |
| 6,867,248 B1 | 3/2005 | Martin et al. | 2005/0025809 A1 | 2/2005 | Hasirci et al. |
| 6,867,249 B2 | 3/2005 | Lee et al. | 2005/0043759 A1 | 2/2005 | Chanduszko |
| 6,921,410 B2 | 7/2005 | Porter | 2005/0080430 A1 | 4/2005 | Wright et al. |
| 6,936,058 B2 | 8/2005 | Forde et al. | 2005/0113868 A1 | 5/2005 | Devellian et al. |
| 7,022,102 B2 | 4/2006 | Paskar | 2005/0131341 A1 | 6/2005 | McGuckin et al. |
| 2001/0014800 A1 | 8/2001 | Frazier et al. | 2005/0267523 A1 | 12/2005 | Devellian et al. |
| 2001/0025132 A1 | 9/2001 | Alferness et al. | 2005/0273135 A1 | 12/2005 | Chanduszko et al. |
| 2001/0034537 A1 | 10/2001 | Shaw et al. | 2005/0288786 A1 | 12/2005 | Chanduszko |
| 2001/0034567 A1 | 10/2001 | Allen et al. | 2006/0122647 A1 | 6/2006 | Callaghan et al. |
| 2001/0037129 A1 | 11/2001 | Thill | 2006/0265004 A1 | 11/2006 | Callaghan et al. |
| 2001/0039435 A1 | 11/2001 | Roue et al. | 2007/0010851 A1 | 1/2007 | Chanduszko et al. |
| 2001/0039436 A1 | 11/2001 | Frazier et al. | 2007/0167981 A1 | 7/2007 | Opolski |
| 2001/0041914 A1 | 11/2001 | Frazier et al. | | | |
| 2001/0041915 A1 | 11/2001 | Roue et al. | | | |
| 2001/0044639 A1 | 11/2001 | Levinson | | | |
| 2001/0049492 A1 | 12/2001 | Frazier et al. | | | |
| 2002/0010481 A1 | 1/2002 | Jayaraman | EP | 0 474 887 | 3/1992 |
| 2002/0019648 A1 | 2/2002 | Akerfeldt et al. | EP | 0 839 549 A | 5/1998 |
| | | | EP | 0 861 632 | 9/1998 |

FOREIGN PATENT DOCUMENTS

| | | |
|---|---|---|
| EP | 1 013 227 | 6/2000 |
| EP | 1 046 375 | 10/2000 |
| EP | 1 222 897 | 7/2002 |
| WO | WO 96/25179 | 8/1996 |
| WO | WO-96/25179 | 8/1996 |
| WO | WO 96/31157 | 10/1996 |
| WO | WO-98/07375 A1 | 2/1998 |
| WO | WO-98/08462 | 3/1998 |
| WO | WO-98/16174 | 4/1998 |
| WO | WO-98/29026 A | 7/1998 |
| WO | WO-98/51812 | 11/1998 |
| WO | WO-99/05977 A1 | 2/1999 |
| WO | WO-99/18862 A1 | 4/1999 |
| WO | WO-99/18864 A1 | 4/1999 |
| WO | WO-99/18870 A1 | 4/1999 |
| WO | WO-99/18871 A1 | 4/1999 |
| WO | WO-99/30640 | 6/1999 |
| WO | WO 00/27292 | 5/2000 |
| WO | WO 00/44428 | 8/2000 |
| WO | WO-01/08600 | 2/2001 |
| WO | WO-01/19256 | 3/2001 |
| WO | WO-01/21247 A1 | 3/2001 |
| WO | WO-01/28432 | 4/2001 |
| WO | WO-01/30268 A1 | 5/2001 |
| WO | WO 01/49185 | 7/2001 |
| WO | WO-01/78596 A1 | 10/2001 |
| WO | WO-01/93783 | 12/2001 |
| WO | WO-02/17809 A1 | 3/2002 |
| WO | WO 02/24106 | 3/2002 |
| WO | WO-03/024337 | 3/2003 |
| WO | WO-03/053493 A | 7/2003 |
| WO | WO-03/53493 A2 | 7/2003 |
| WO | WO-03/059152 | 7/2003 |
| WO | WO-03/063732 A | 8/2003 |
| WO | WO 03/077733 | 9/2003 |
| WO | WO-03/082076 | 10/2003 |
| WO | WO-03/103476 A | 12/2003 |
| WO | WO-2004/032993 | 4/2004 |
| WO | WO-2004/037333 | 5/2004 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Kimura, A., et al., "Effects of Neutron Irradiation on the Transformation Behavior in Ti-Ni Alloys," Abstract, Proceedings of the Int'l Conf. On Mariensitic Transformations (1992) pp. 935-940.

Nat'l Aeronautics and Space Administration, "55-Nitinol—The Alloy with a Memory: Its Physical Metallurgy, Properties, and Applications," A Report, pp. 24-25.

Ramanathan, G., et al., "Experimental and Computational Methods for Shape Memory Alloys," 15$^{th}$ ASCE Engineering Mechanics Conf., Jun. 2-5, 2003.

Ruiz et al. "The Puncture Technique: A New Method for Transcatheter Closure of Patent Foramen Ovale," Catheterization and Cardiovascular Interventions 53, Wiley-Liss, Inc., 2001, pp. 369-372.

Shabalovskaya, S., "Surface, corrosion and biocompatibility aspects of Nitinol as an implant material," Bio-Medical materials and Engineering, (2002) vol. 12, pp. 69-109.

SMST-2000, "Proceedings of the International Conference on Shape Memory and Superelastic Technologies," Apr. 30 to May 4, 2000, Asilomar Conference Center.

Stöckel, "Nitinol Medical Devices and Implants," SMST-2000 Conference Proceedings, 2001, pp. 531-541.

Uchil, J. "Shape Memory Alloys—Characterization Techniques," Pramana—Journal of Physics, (2002) vol. 58, Nos. 5 & 6, pp. 1131-1139.

Meier, MD, Bernhard et al., "Contemporary Management of Patent Foramen Ovale," American Heart Association, Inc., Circulation, 2003, vol. 107, pp. 5-9.

Athanasion, T., "Coronary Artery Bypass with the Use of a Magnetic Distal Anastomotic Device: Surgical Technique and Preliminary Experience," The Heart Surgery Forum #2004-1024, 2004, 4 pgs.

Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.

Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.

Filsoufi, F., et al., "Automated Distal Coronary Bypass with a Novel Magnetic Coupler (MVP system)," J. Thoracic and Cardiovascular Surgery, vol. 127(1), pp. 185-192.

International Search Report, International Application No. PCT/US02/40850 mailed Jun. 19, 2003 (4 pgs).

International Search Report, International Application No. PCT/US03/01050, mailed Jul. 8, 2003 (1 pg).

International Search Report, International Application No. PCT/US03/09051, mailed Sep. 29, 2003 (2 pgs).

International Search Report, International Application No. PCT/US03/17715, mailed Mar. 24, 2004 (2 pgs).

International Search Report, International Application No. PCT/US03/32133, mailed Apr. 22, 2004 (1 pg).

International Search Report, International Application No. PCT/US03/34003 mailed Oct. 3, 2004 (4 pgs).

International Search Report, International Application No. PCT/US03/35479, mailed Apr. 14, 2004 (2 pgs).

International Search Report, International Application No. PCT/US03/35998 mailed Jun. 16, 2004 (5 pgs).

International Search Report, International Application No. PCT/US03/39253, mailed Apr. 19, 2004 (4 pgs).

International Search Report, International Application No. PCT/US04/022643, mailed Mar. 31, 2005 (2 pgs).

International Search Report, International Application No. PCT/US04/026998, mailed Apr. 22, 2005 (5 pgs).

International Search Report, International Application No. PCT/US04/029978, mailed Jan. 26, 2005 (3 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US05/015382, mailed Oct. 6, 2005 (4 pgs).

International Search Report, International Application No. PCT/US06/009978, mailed Jul. 13, 2006 (2 pgs).

International Search Report, International Application No. PCT/US2007/065541, mailed Aug. 7, 2007 (4 pgs).

International Search Report, International Application No. PCT/US97/14822, mailed Feb. 20, 1998 (2 pgs).

International Search Report, International Application No. PCT/US97/17927, mailed Feb. 10, 1998 (1 pg).

Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.

Klima, U., "Magnetic Vascular Port in Minimally Invasive Direct Coronary Artery Bypass Grafting," Circulation, 2004, II-55-II-60.

Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.

Ruddy, A.C. et al., "Rheological, Mechanical and Thermal Behaviour of Radipaque Filled Polymers", *Polymer Processing Research Centre, School of Chemical Engineering*, Queen's University of Belfast, 5 pages.

Stein, H., "Telemanipulator-gestützte Applikation eines magnetischen Gefäβ-Kopplers am schlagenden Herzen mit dem da Vinci™ -Surgical-System," Biomedizinische Technik, 2003, vol. 48(9), pp. 230-234.

Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.

International Search Report, International Application No. PCT/US03/17390, mailed Oct. 6, 2003 (4 pgs).

International Search Report, International Application No. PCT/US2007/065526, mailed Aug. 8, 2007 (5 pgs).

European Examination Report, European Application No. 04781644.2, mailed Aug. 23, 2007 (3 Pages).

International Search Report, International Application No. PCT/US05/34276, mailed Oct. 9, 2007.

European Search Report, European Application No. 03729663.9, mailed Feb. 20, 2008 (3 Pages).

European Examination Report, European Application No. 03779297.5, mailed Mar. 15, 2007 (6 Pages).

International Search Report, International Application No. PCT/US2006/009978, mailed Jul. 13, 2006 (2 pgs).

International Search Report and Written Opinion, International Patent Application No. PCT/US08/59448, mailed Sep. 5, 2008 (8 pages).

International Search Report and Written Opinion, International Patent Application No. PCT/US08/60738, mailed Sep. 3, 2008 (10 pages).

\* cited by examiner

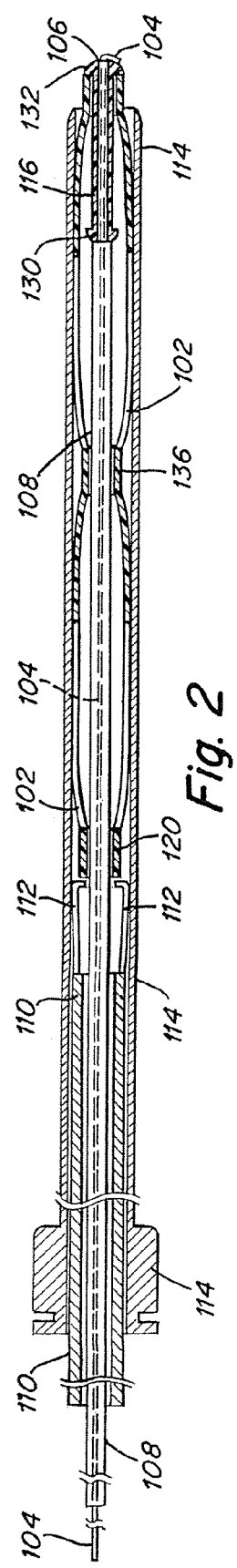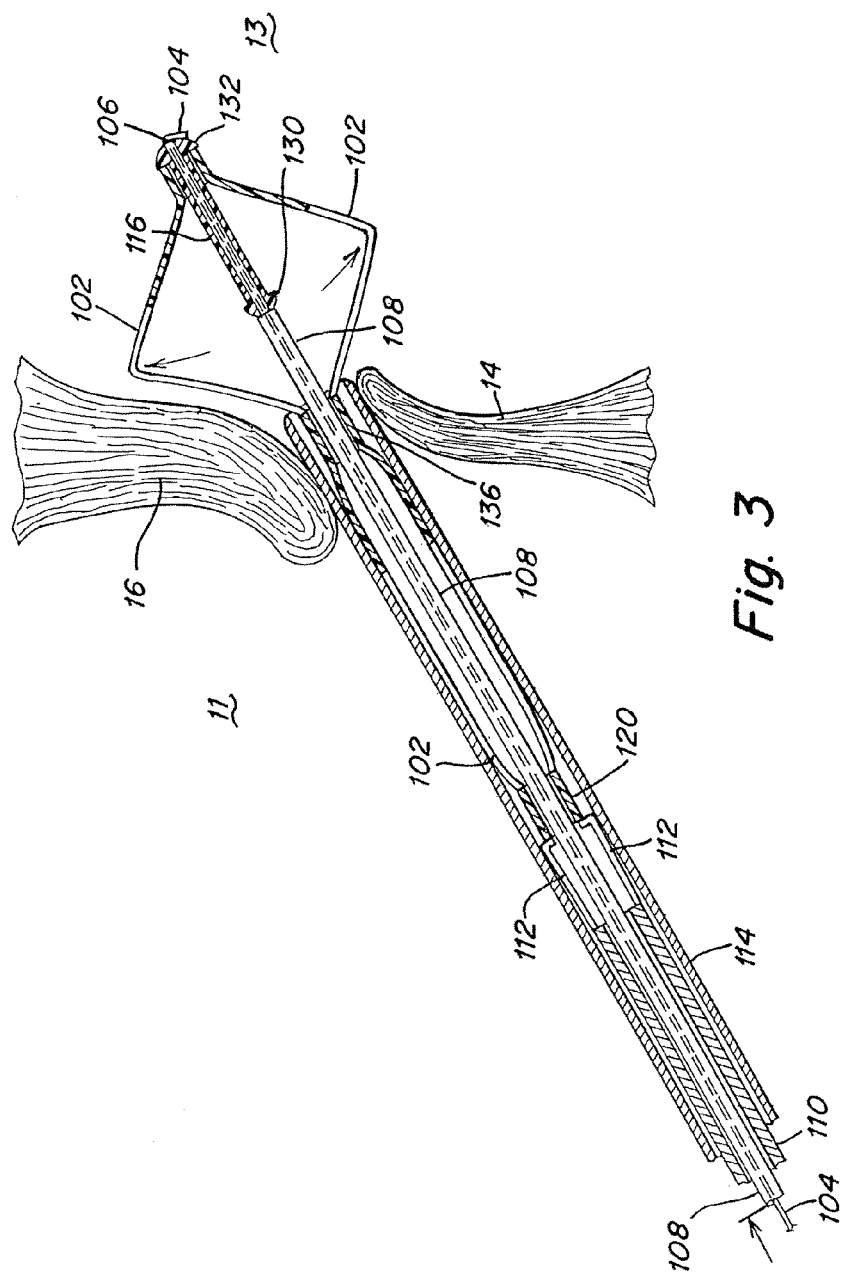

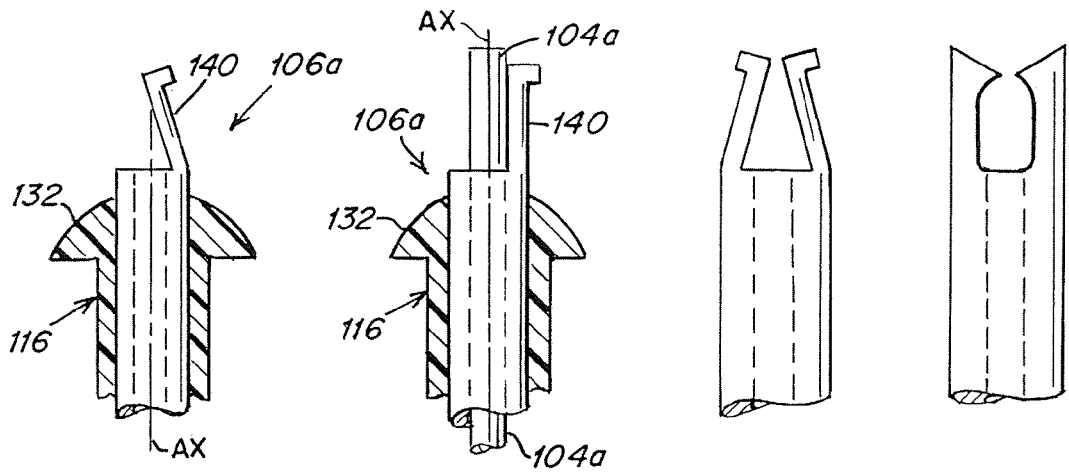
*Fig. 18a*  *Fig. 18b*  *Fig. 19a1*  *Fig. 19a2*
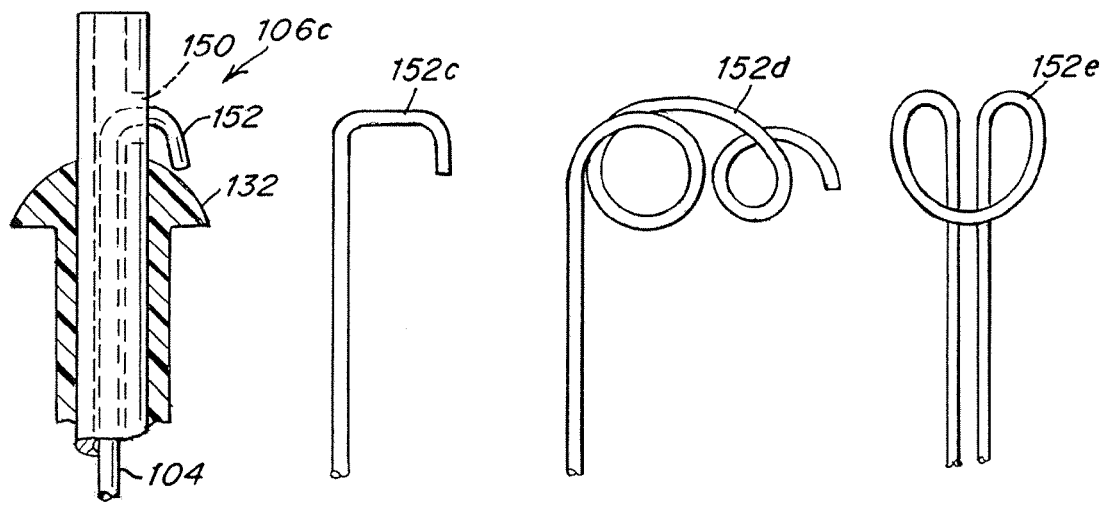
*Fig. 19b*  *Fig. 19c*  *Fig. 19d*  *Fig. 19e*
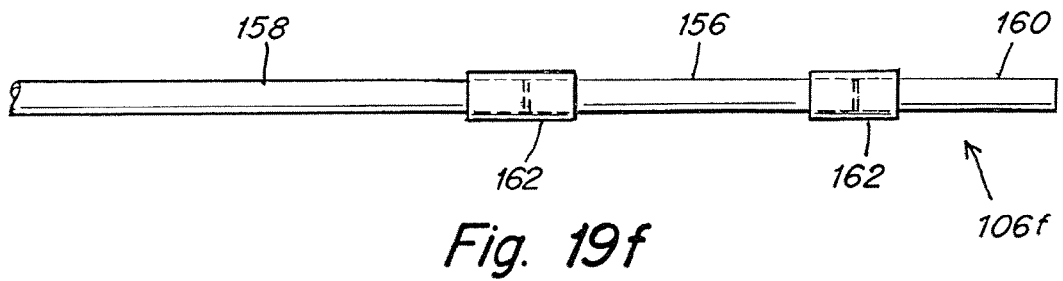
*Fig. 19f*

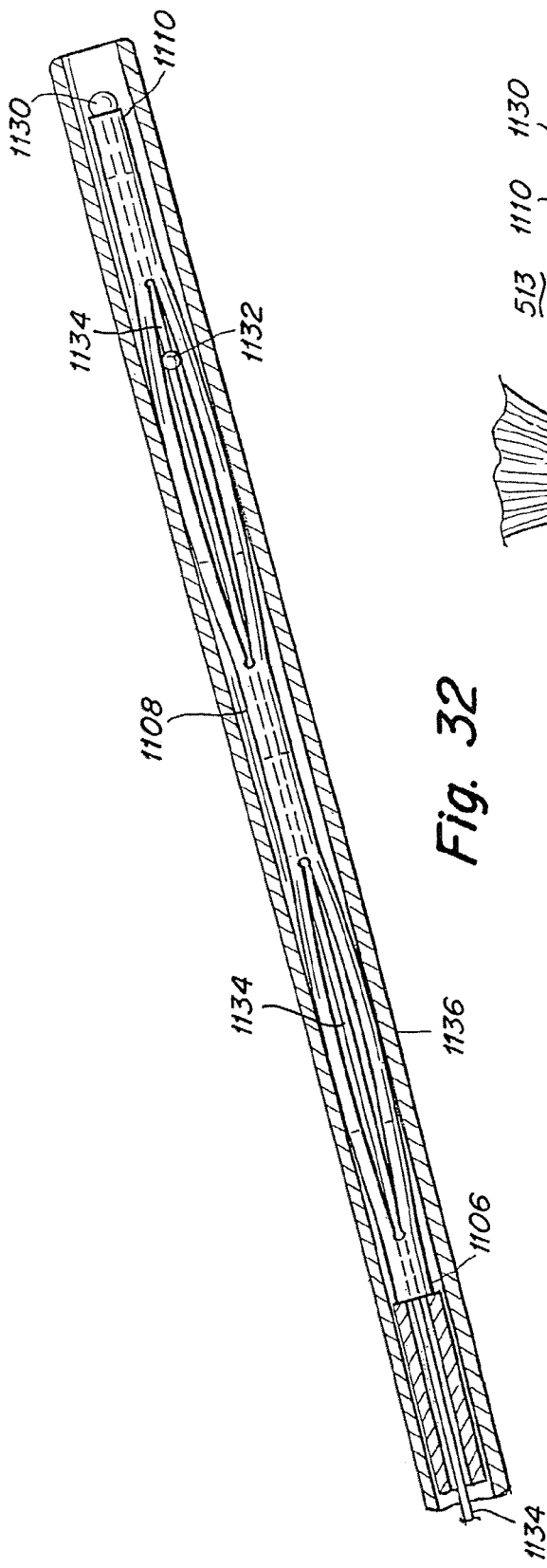
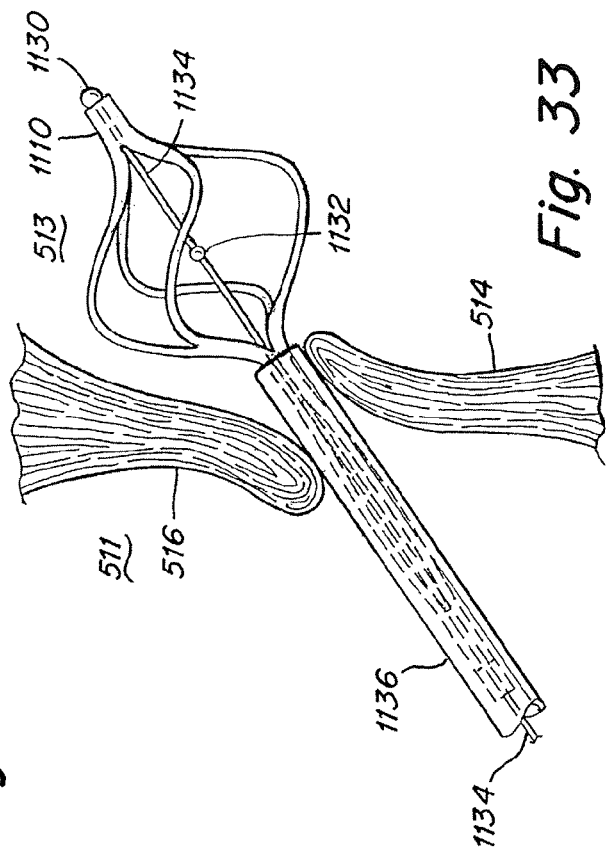
Fig. 32
Fig. 33

DELIVERY/RECOVERY SYSTEM FOR SEPTAL OCCLUDER

CROSS-REFERENCE TO RELATED APPLICATION

This application claims priority to provisional application Ser. No. 60/549,741, filed Mar. 3, 2004, and 60/569,422, filed May 7, 2004, each of which is incorporated herein by reference.

BACKGROUND

The present invention relates generally to an occlusion device for the closure of physical anomalies like septal apertures, such as patent foramen ovale and other septal and vascular defects.

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating. Because blood is oxygenated through the umbilical cord, and not through the developing lungs, the circulatory system of a heart in a fetus allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

SUMMARY

Embodiments of a delivery/recovery system allow an operator to deploy and, in many cases, recover a medical implant, such as an occluder for closing a PFO. In one embodiment, the system includes a delivery mandrel for preventing the occluder from moving in the proximal direction, a delivery wire for securing the occluder to the delivery mandrel and preventing unwanted movement in the distal direction, and a sheath for enveloping the delivery wire, mandrel and occluder. By moving the sheath relative to the occluder in a series of steps, the occluder opens first on a distal side and then on a proximal side, in a manner that locks the occluder in place.

In this embodiment, the system preferably further includes a recovery catheter with claws that can be controlled to grasp a partially deployed occluder and withdrawing the occluder back into the sheath for repositioning or removal.

A handle can be provided for assisting the operator with manipulations to deliver and/or recover an occluder. The handle can include springs for biasing the mandrel and sheath, with knobs for holding these components in desired positions.

The system can be used with a PFO occluder, such as an occluder with a center joint for passing through the PFO tunnel, and closure components on the distal (left atrial) side and on the proximal (right atrial) side. The closure components can include loops, open ended struts, or struts that double back from the center joint to an end of the occluder. The occluder preferably also has a catching structure for holding the components in place. The occluder can be made of a polymer, nitinol, stainless steel, or other suitable material, and can include a fabric for promoting tissue growth.

The delivery/recovery system in the preferred embodiment provides a convenient mechanism for delivering the occluder or other device, and for recovering the device as needed. Other features and advantages will become apparent from the following detailed description and drawings.

BRIEF DESCRIPTION OF DRAWINGS

FIG. 2 is a cross-section of a clover leaf occluder and a delivery/recovery system in its "stowed" configuration;

FIGS. 3, 4, 5a, 5b and 5c are cross-sectional views that illustrate a sequence of events for using the recovery/delivery system to deploy the clover leaf occluder within the PFO;

FIGS. 18a and 18b show another embodiment of the mandrel tip;

FIG. 19a shows several alterative embodiments of the mandrel tip;

FIG. 19b shows another alternative embodiment of the mandrel tip;

FIGS. 19c through 19e show several embodiments of the distal end of the wire for use with the mandrel tip of FIG. 19b;

FIG. 19f shows a mandrel with a soft segment added near its distal end;

FIG. 32 through 39 show several views of another occluder;

DESCRIPTION OF INVENTION

The described embodiment is a delivery/recovery system for deploying and/or removing a device for occluding an aperture within body tissue. In particular and as described in detail below, an occluder may be used for closing a PFO in the atrial septum of a heart. Application Ser. No. 10/890,784, filed Jul. 14, 2004, which is incorporated herein by reference, provides a more detailed description of an occluder that the described embodiment manipulates. This occluder has a center joint, opposite ends, and loops extending from the center joint to the ends such that the loops are generally parallel to the PFO tunnel. Because of its shape, the occluder is referred to as a "clover leaf" occluder.

Although the embodiments described herein refer to a PFO in particular, the devices and methods of these embodiments may be used to treat other anatomical conditions, such as an atrial septal defect (ASD) or ventricular septal defect (VSD). As such, the invention should not be considered limited to any particular anatomical condition. Similarly, although the embodiments described herein refer to a clover leaf occluder in particular, the devices and methods of these embodiments may be used to deploy other occluders, and other implants in general. As such, the invention should not be considered limited to any particular deployable implants. For example, an occluder can include struts that extend out in a manner like an umbrella, or can have struts that double back from a center joint to ends, with loops that are perpendicular to the PFO tunnel. As used herein, the term "operator" means the person operating the delivery/recovery system to insert an occluder into the body of a patient.

Figure 1:
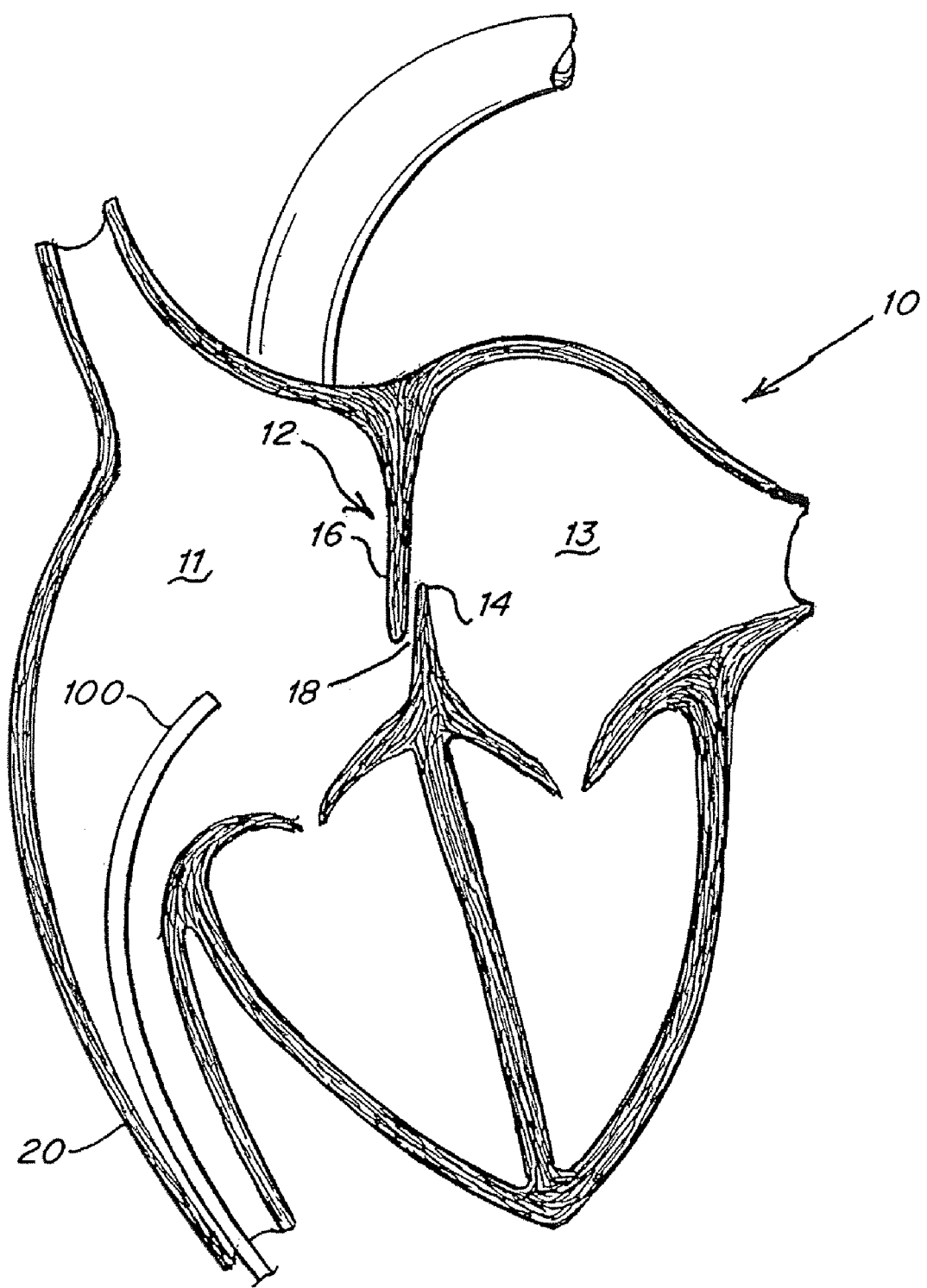
FIG. 1 shows a human heart with anatomical structures relevant to this description.
Figure 4:
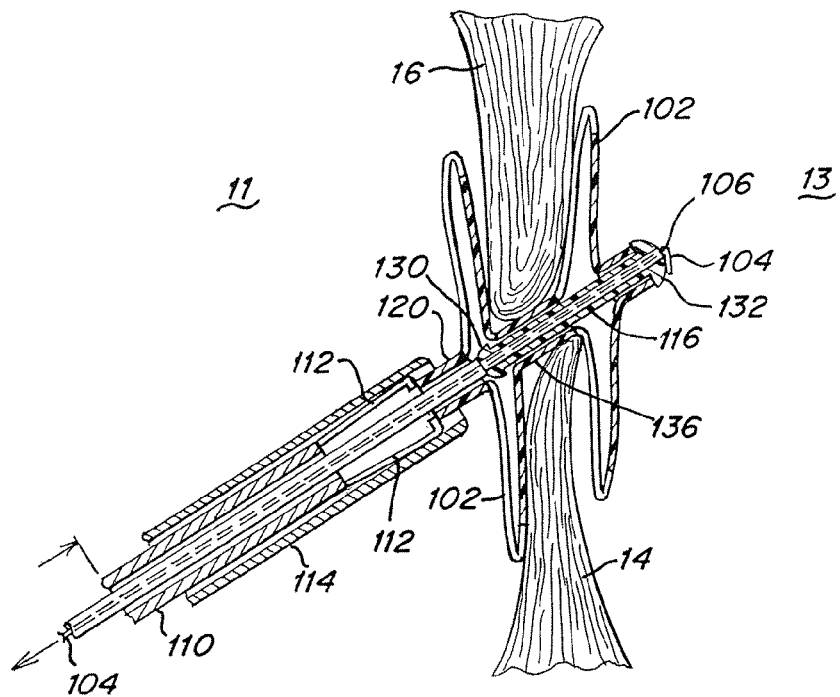

FIG. 1 illustrates a human heart 10, having a right atrium 11 and a left atrium 13. The atrial septum 12 includes septum primum 14, septum secundum 16, and a passage 18 between the right atrium 11 and left atrium 13. The anatomy of the septum varies widely within the population. In some people, septum primum 14 extends to and overlaps with septum secundum 16. The septum primum 14 may be quite thin. When a PFO is present, there is a chance that blood could travel through the passage 18 between septum primum 14 and septum secundum 16 (referred to as "the PFO tunnel"). FIG. 1 further shows an outline of the delivery/recovery system 100, described herein, being inserted into the right atrium 11 through the inferior vena cava 20.

As shown in FIG. 2, a clover leaf occluder delivery/recovery system 100 includes a clover leaf occluder 102, a delivery wire 104, a mandrel tip 106, a mandrel 108, a recovery catheter 110, recovery claws 112, a delivery/recovery sheath 114, and a catch member 116 of the clover leaf occluder. The delivery/recovery system also includes a handle (not shown) that enables the operator to repeatably and efficiently perform the steps described herein. The handle is described in more detail in the sections to follow. The occluder 102 and all components of the delivery/recovery system 100 may be advanced into the sheath 114 after the sheath 114 has crossed the PFO 18, and the guide wire has been removed from the sheath 114.

FIG. 2 shows the clover leaf occluder delivery/recovery system 100 in its "stowed" configuration, i.e., as it is arranged when it is ready to be inserted into a patient. The delivery wire 104, the mandrel 108, the recovery catheter 110, and the delivery/recovery sheath 114 are all disposed in a coaxial arrangement about a longitudinal central axis, with the mandrel 108 disposed about the delivery wire 104, the recovery catheter 110 disposed about the mandrel 108, and the delivery/recovery sheath 114 disposed about the recovery catheter 110. The mandrel tip 106 refers to the distal end of the mandrel 108. The mandrel 108 extends through the occluder 102 so that the mandrel tip 106 is disposed at the distal end of the catch member 116. The delivery wire extends through the mandrel and out of the mandrel tip 106, and is bent at its distal end to form a hook. The bent end of the delivery wire rests against the distal end of the locking member and provides a restraining force for preventing the catch member 116 from moving in the distal direction.

In one embodiment, the mandrel 108 includes a portion at the distal end that has a smaller outside diameter, creating a shoulder at the transition. The smaller outside diameter portion fits through the catch member 116, and the shoulder provides a stop against which the proximal end of the catch member 116 rests. The shoulder therefore prevents movement of the catch member 116 in the proximal direction. In an alternative embodiment, the mandrel 108 has an outside diameter slightly less than the inside diameter of the locking member, and includes a region having an extended outside diameter for providing a stop (i.e., a bump) against which the proximal end of the locking member 116 rests, to prevent movement of the catch member in the proximal direction.

The recovery claws 112 are attached to the distal end of the recovery catheter 110, and are spring loaded to tend toward opening, i.e., expansion away from the central axis. The distal end of the catch member 116 is fixedly attached to the distal end of the occluder 102.

Figure 15:
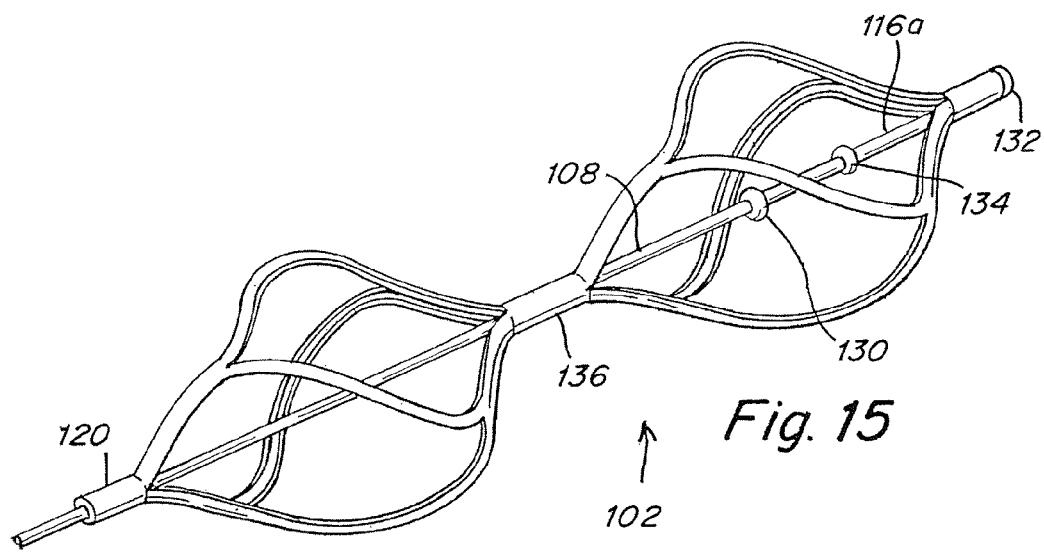
FIGS. 15, 16 and 17 show an occluder with a locking member as in FIG. 13, in three stages of deployment.

FIGS. 3, 4, 5a, 5b and 5c illustrate a sequence of events for using the recovery/delivery system 100 to deploy the clover leaf occluder 102 within the PFO tunnel 18. FIG. 3 shows a sheath 114 inserted into the PFO tunnel, with the occluder 102 partially deployed on the left atrial side of the PFO tunnel 18. The operator causes the occluder 102 to exit the sheath 114 by moving the sheath relative to the occluder, preferably by pulling the sheath 114 away from the distal end, while maintaining the mandrel 108 and delivery wire 104 relatively fixed. Once the sheath 114 uncovers approximately one half of the occluder 102, the clover petals of the occluder 102 are free to expand away from the central axis on the left atrial side of the PFO 18. The operator pushes the sheath relative to the mandrel 108 and the wire 104, further forcing the clover petals open to extend outwardly in a radial direction (an example in partially deployed form is shown in FIG. 15, with full deployment in FIG. 17). This movement also pushes a central portion 136 of the occluder 102 over the larger diameter proximal end 130 of the locking member.

Referring to FIG. 4, the operator again moves the sheath 114 relative to the mandrel 108 and the wire 104, preferably by pulling back on the sheath 114, thereby uncovering the proximal petals of the occluder 102 in the right atrium 11 and allowing these petals to expand away from the central axis. The operator then pushes the sheath 114 relative to the mandrel 108 and wire 104 further forcing those clover petals to extend outwardly in a radial direction on the right atrial 11 side of the PFO 18. The operator continues to push the sheath relative to the mandrel 108 and wire 104, forcing the proximal end of the occluder over the proximal end of the catch member 116, thereby holding the occluder 102 in its deployed position.

Figure 5A:
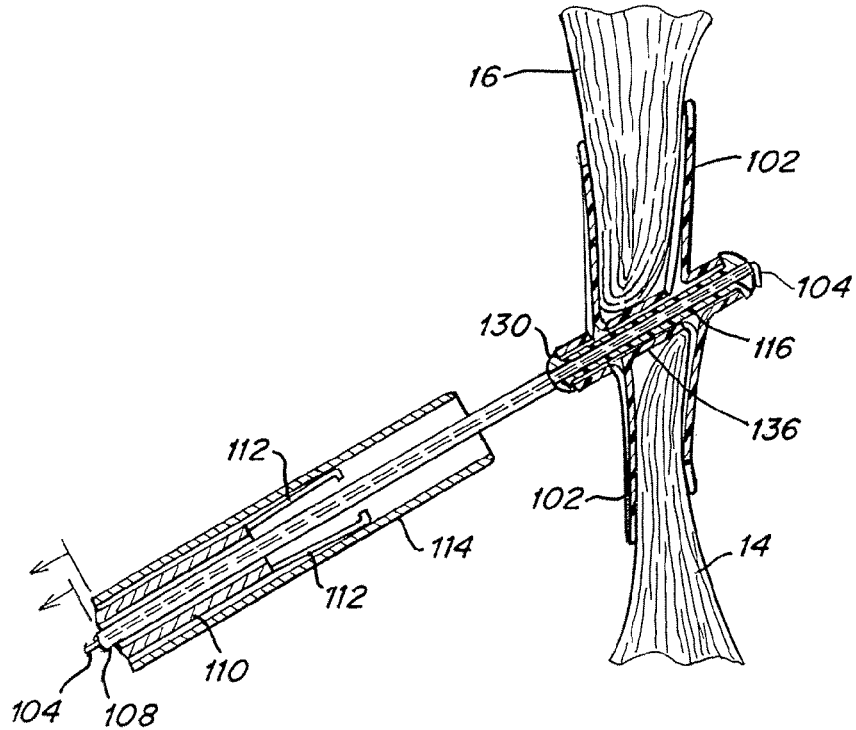
Figure 5B:
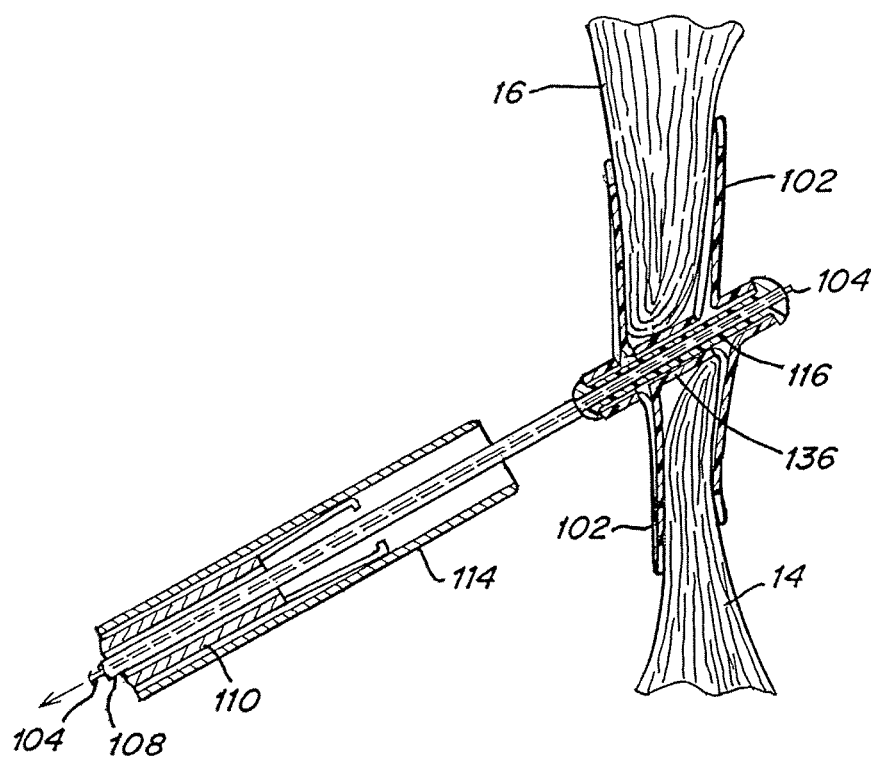
Figure 5C:
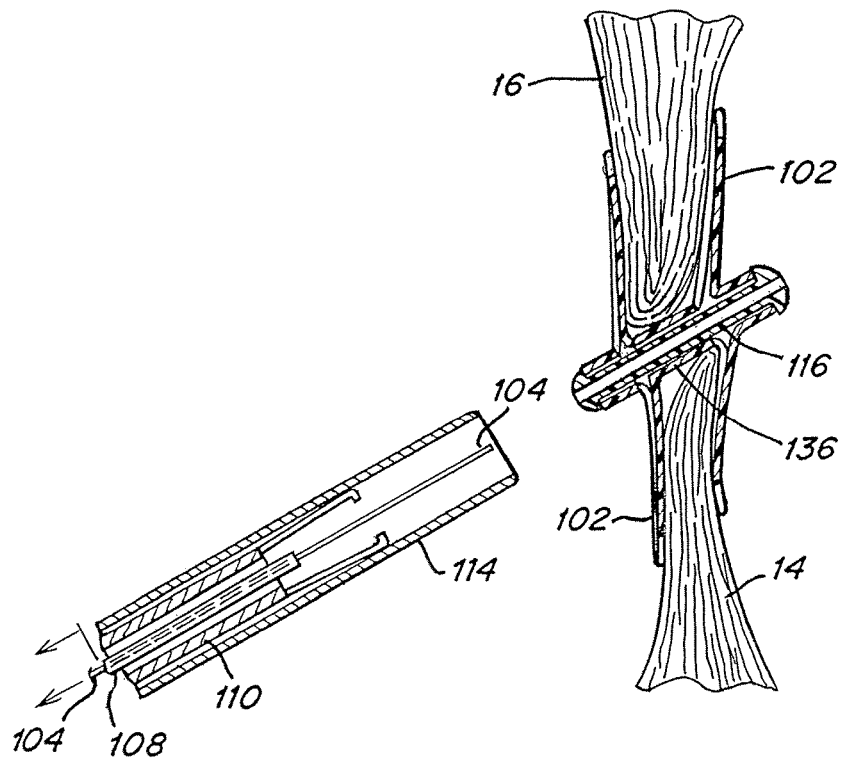

At this time the operator pulls the sheath 114 relative to the mandrel 108, away from the deployed occluder 102, as shown in FIG. 5a. Withdrawing the sheath 114 from the occluder 102 provides the flexibility necessary to pivot the occluder 102 via the mandrel 108 to a desired position. The operator can then determine whether the occluder 102 is properly deployed with respect to the PFO tunnel 18, using techniques such as transesophageal or intracardiac echo, and/or fluoroscopy. If the operator deems the occluder 102 to be properly deployed, the operator pulls on the delivery wire 104 while holding the mandrel 108 in a fixed position. If the operator pulls the delivery wire 104 with sufficient force, the bend at the distal end of the delivery wire 104 straightens against the mandrel tip 106, and the wire 104 withdraws into the mandrel 108 (FIG. 5b). Once the bend in the distal end of the wire 104 is gone, there is no longer a restraining force preventing the catch mechanism 116 from moving in the distal direction, and the operator disengages the mandrel 108 from the catch member 116 (FIG. 5c). Alternatively, the operator could straighten the bend in the wire 104 by holding the delivery wire 104 in a fixed position and pushing on the mandrel 108, or by a combination of pulling on the wire 104 and pushing on the mandrel 108.

Figure 6:
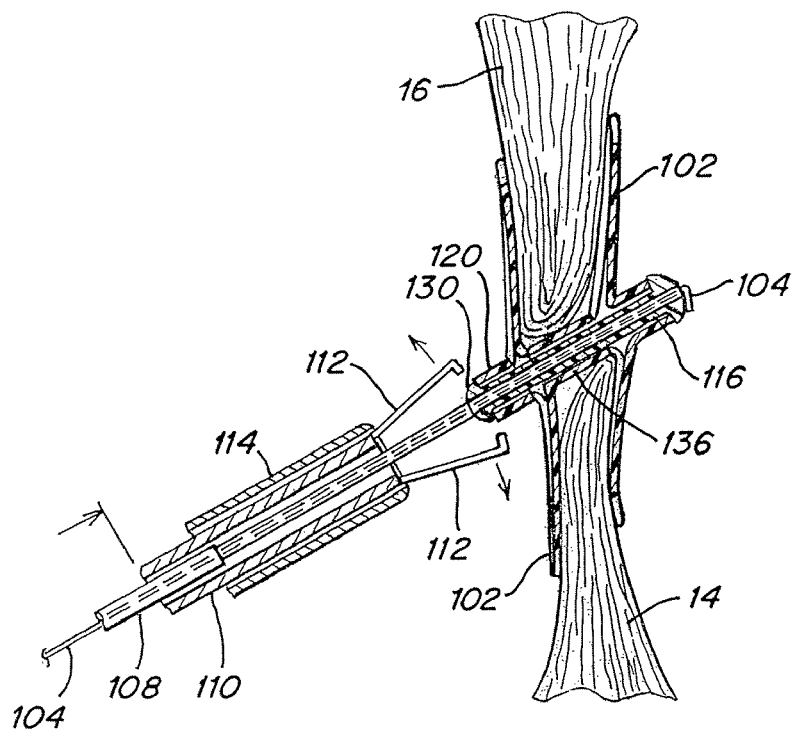
FIGS. 6, 7, 8, 9, 10 and 11 are cross-sectional views that illustrate a sequence of events for using the delivery/recovery system to recover a deployed occluder.
Figure 7:
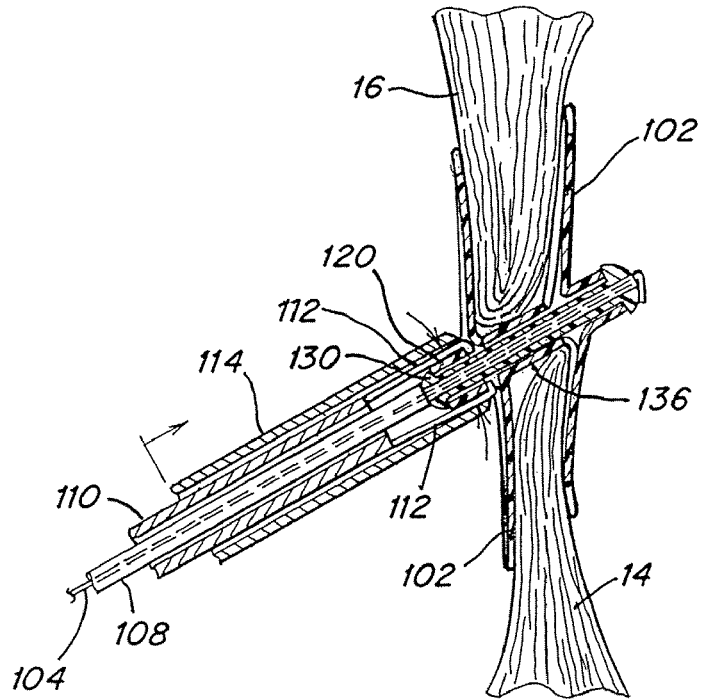

If, after withdrawing the sheath 114 and manipulating the occluder 102 as described above (FIG. 5*a*), the operator decides the occluder 102 is not properly deployed, the operator can perform a recovery and/or repositioning procedure. FIGS. 6 through 11 illustrate a sequence of steps described in detail below. From the position shown in FIG. 5*a*, the operator pushes longitudinally on the recovery catheter 110 with respect to the sheath 114. Doing so causes the sheath 114 to uncover the recovery claws 112, removing a restricting force from the spring-loaded recovery claws 112, and allowing the claws 112 to expand away from the central axis, as shown in FIG. 6. The operator continues to push the recovery catheter 110 relative to the sheath until the claws 112 surround the proximal end of the occluder 102. The operator then pushes the sheath 114 longitudinally relative to the recovery catheter 110 until the sheath covers the claws 112, thereby closing the claws 112 on the proximal end of the occluder 102, as shown in FIG. 7.

Figure 8:
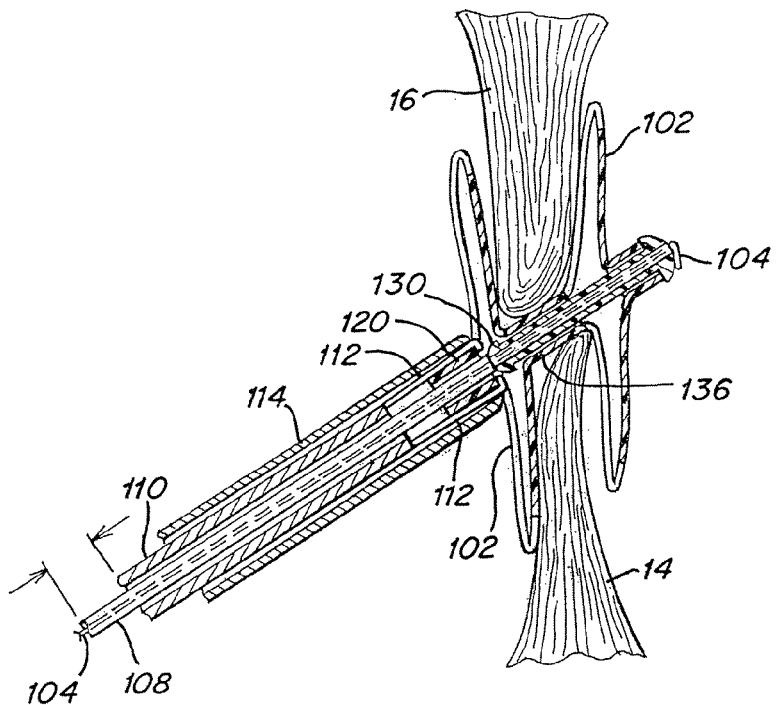
Figure 9:
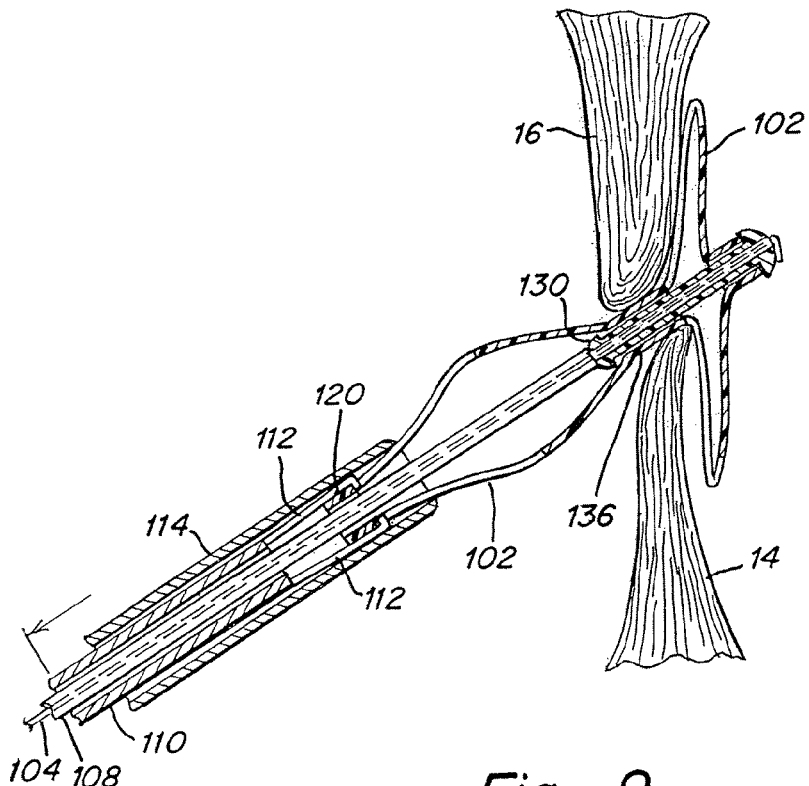
Figure 10:
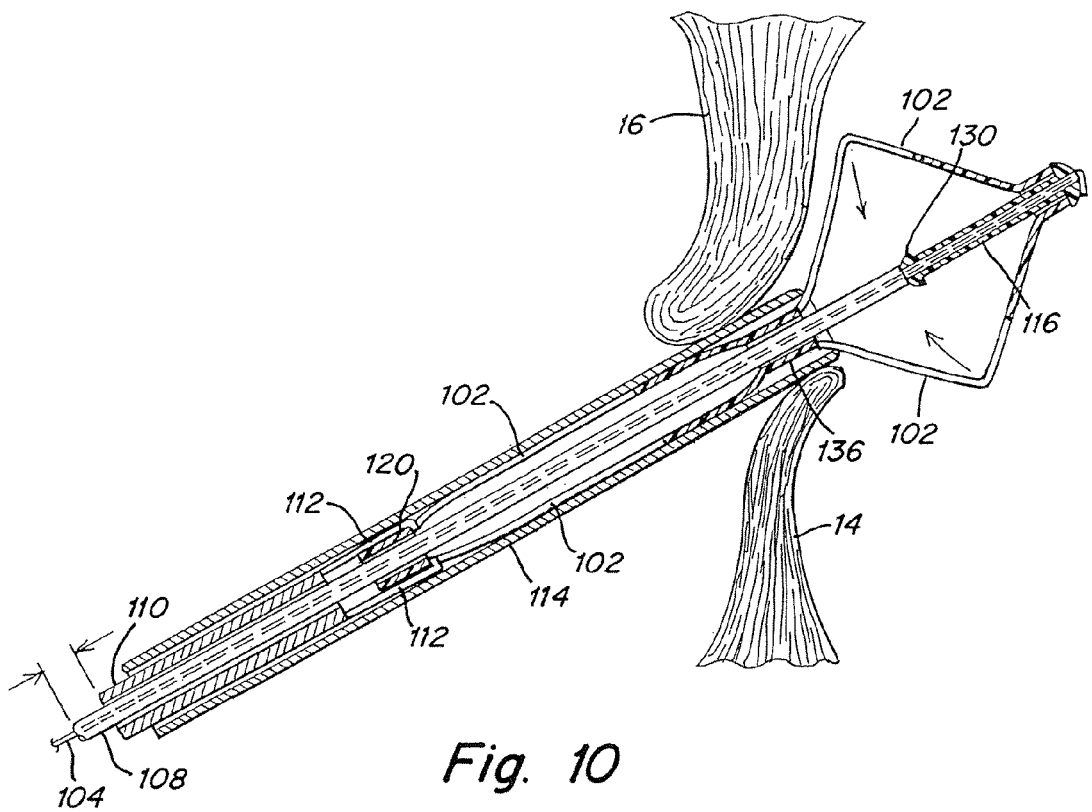

With the claws 112 immobilizing the occluder 102 relative to the recovery catheter 110, the operator pushes the mandrel 108 longitudinally relative to the recovery catheter 110, forcing the proximal stop 130 of the catch member 116 through the proximal end of the occluder 102 in a distal direction, as shown in FIG. 8. As the operator continues to push the mandrel 108 relative to the recovery catheter 110, the mandrel 108 pushes the proximal stop 130 of the catch member 116 through the occluder center joint 136, and the occluder elongates, so that the clover petals of the occluder retract toward the central axis, as shown in FIGS. 9 and 10. The operator pulls the recovery catheter 110 longitudinally relative to the sheath 114, so that the claws 112 pull the elongated occluder 102 back into the sheath 114. Once the sheath 114 covers the occluder 102, as shown in FIG. 11, the operator can remove the delivery/recovery system 100 from the patient.

Figure 11:
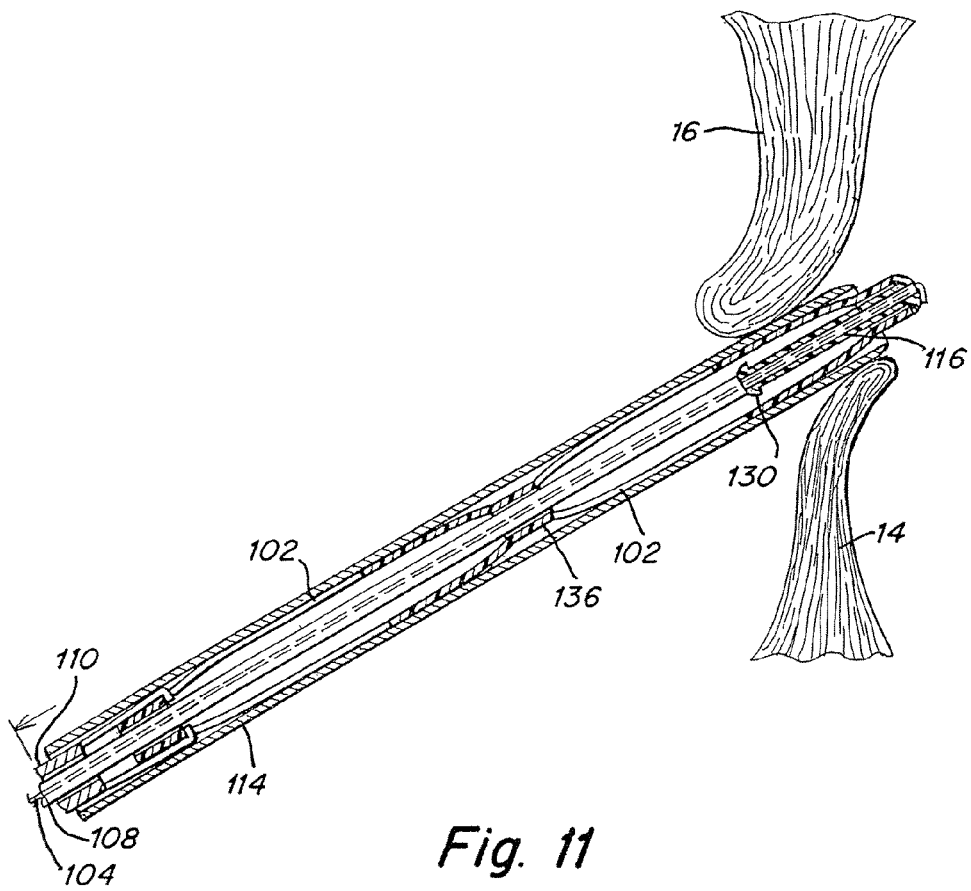

During this process, such as at points shown in FIG. 9, FIG. 10 or FIG. 11, the operator can reverse course and deploy again as in the manner described in conjunction with FIGS. 3 through 5*c*.

Figure 12:
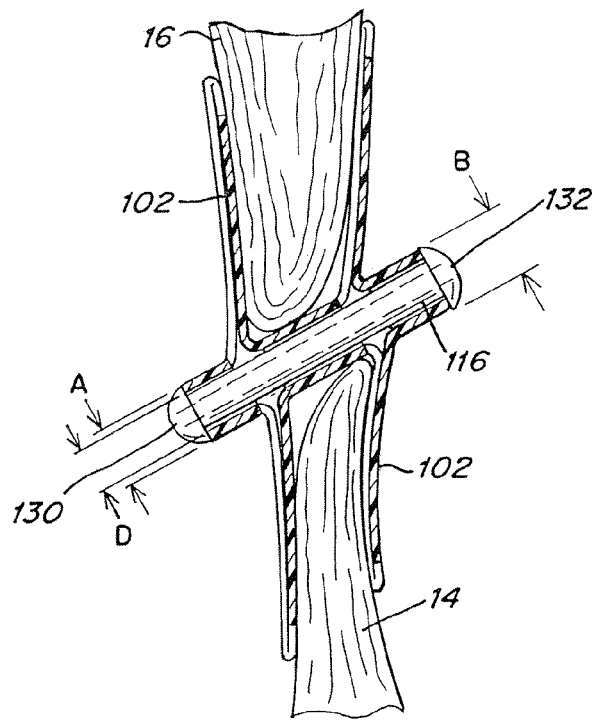
FIG. 12 shows an occluder deployed as described herein.

FIG. 12 shows an occluder 102 deployed as described above. The catch member 116 in this embodiment includes a proximal stop 130 and a distal stop 132. The diameter A of the proximal stop 130 is greater than the inside diameter D of the occluder 102, and the diameter B of the distal stop 132 is greater than the diameter A of the proximal stop 130. As described herein, distal stop 132 should be fixedly connected to the rest of the occluder and thus should not be movable with respect to the end of the occluder at any time, while the portions of the occluder move over the proximal end to lock the occluder in place.

Figure 13:
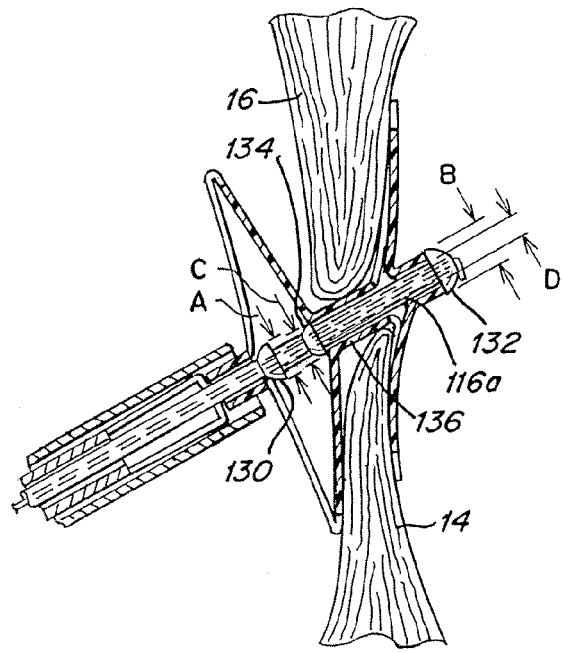
FIGS. 13 and 14 show an occluder with a locking member having a third stop between the end stops.
Figure 14:
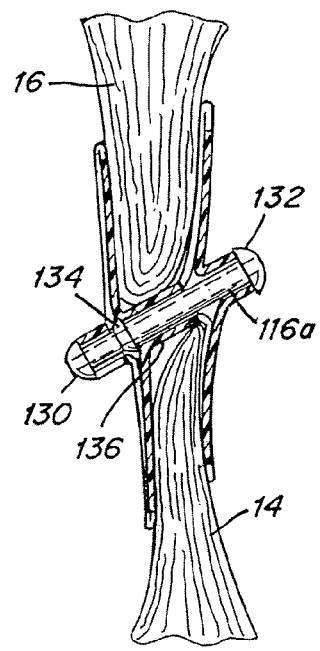

Referring to FIGS. 13 and 14, in another embodiment, the catch member 116*a* has a third stop 134 between the proximal stop 130 and the distal stop 132. The third stop 134 provides an intermediate stop for the center joint 136 of the occluder 102. The diameter A of the proximal stop 130 is greater than the inside diameter D of the occluder 102, the diameter B of the distal stop 132 is greater than the diameter A of the proximal stop 130, and the diameter C of the intermediate stop 134 is approximately equal to the proximal stop 130. The third stop 134 allows the distal petals 138 of the occluder 102 to maintain their form prior to the engagement of the proximal stop 130, and in the event the proximal stop 130 fails.

Figure 16:
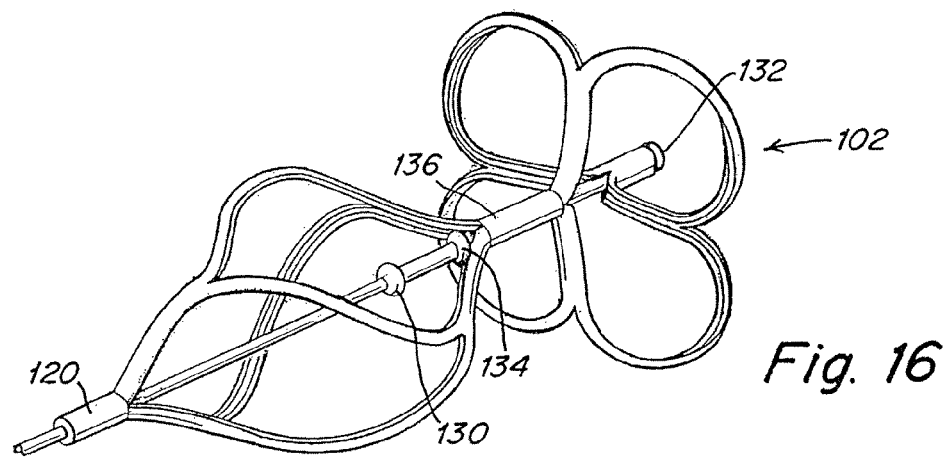
Figure 17:
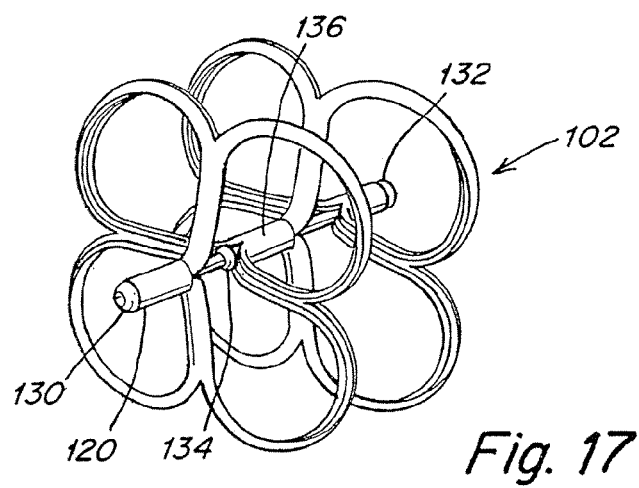

FIGS. 15, 16 and 17 show a clover leaf occluder 102 in three stages of deployment with a three stop catch member 116*a*. FIG. 15 shows the occluder 102 with the distal end against the distal stop 132, FIG. 16 shows the occluder 102 with the center joint locked with the intermediate stop 134, and FIG. 17 shows the occluder 102 completely deployed with the distal end locked against the distal stop 132, the center joint 136 held against the intermediate stop 134, and the proximal end held against the proximal stop 130.

One embodiment includes a self-locking mandrel tip 106*a* as shown in FIGS. 18*a* and 18*b*. This mandrel tip 106*a* eliminates the need for a bend at the end of the delivery wire 104 by including an L-shaped extension 140 that is preferably biased toward the center axis AX. When biased as shown in FIG. 18*a*, the mandrel tip 106*a* can pass relatively unimpeded through the axial passage in the catch member 116. When a straight delivery wire 104*a* is inserted through the mandrel 106*a* as shown in FIG. 18*b*, the wire 104*a* forces the L-shaped extension 140 away from the center axis and beyond the inside diameter envelope of the catch member. In this position, the L-shaped extension 140 impedes passage through the catch member 116, and performs the same function that the bent wire 104 provided in the earlier-described embodiment. Removing the wire 104*a* allows the L-shaped extension 140 to return to its former biased position, again allowing relatively unimpeded passage through the locking member 116.

Other alternative shapes for the mandrel tip 106*a* are shown in FIG. 19*a*. All of these examples allow easier passage through the locking member 116 without a delivery wire 104*a* inserted than with a delivery wire 104*a* inserted, and all of these examples operate without requiring a bend in the distal end of the delivery wire and the associated force required to remove it.

FIG. 19*b* shows another embodiment of a self-catching mandrel tip 106*c* having an aperture 150 in the side wall of the mandrel. The delivery wire 104 passes through this aperture 150 rather than extending out through the distal end of the mandrel as in the previously-described embodiments. The distal end 152 of the delivery wire in this embodiment has a hook that restricts the distal stop 132 of the catch member 116, and/or the distal end of the occluder 102, from movement in the distal direction. Other possible shapes for the distal end 152 of the delivery wire 104 may also be used, for example those shown in FIGS. 19*c*, 19*d* and 19*e*. The shape shown in FIG. 19*e* uses a wire that is thinner than the other embodiments shown, so that a pair of wires pass through the mandrel. When pulling the delivery wire to release the implant from the system 100, the force required to "unbend" the hook is isolated to the rim of the aperture 150. Since the mandrel is preferably made of stainless steel or another similarly hard material, the rim of the aperture 150 can withstand that force without significant deformation.

FIG. 19*f* shows a mandrel with a soft segment 156 added near the distal end of the mandrel to improve pivoting between the delivery system and the implant. In this embodiment, the soft segment is made of a martensitic or R-phase tube segment 156 attached to the proximal portion 158 of the mandrel and the distal portion 160 of the mandrel via any of several appropriate techniques known in the art. For example, a titanium sleeve 162 may be used to attach the segment 156 via welding or crimping to the proximal portion 158 and the distal portion 160 of the mandrel, as shown in FIG. 19*f*. The proximal portion 158 and the distal portion 160 of the mandrel may be made of stainless steel to provide a more cost effective system than having the entire mandrel made of a martensitic or R-phase material (e.g., nitinol). Other metals and/or polymers may alternatively be used to achieve similar results.

In contrast to occlusion devices made of materials such as nitinol, polymers typically produce recovery forces that are low and can be insufficient to bring an implant device (e.g., an occluder) to its desired shape upon delivery without some assistance from the operator. The operator might have to manipulate several elements of the delivery/recovery system. A handle 200 for this embodiment of an occluder delivery/recovery system 100 performs many of these manipulations with minimal input from the operator, so that a polymer may be deployed almost as easily as, and in some cases easier than, a metal device. By carefully controlling and regulating the applied forces, the handle 200 also protects the implant devices from overstressing that can occur with manual manipulations. Elements of the handle also have general applicability to metal implant devices.

Figure 20:
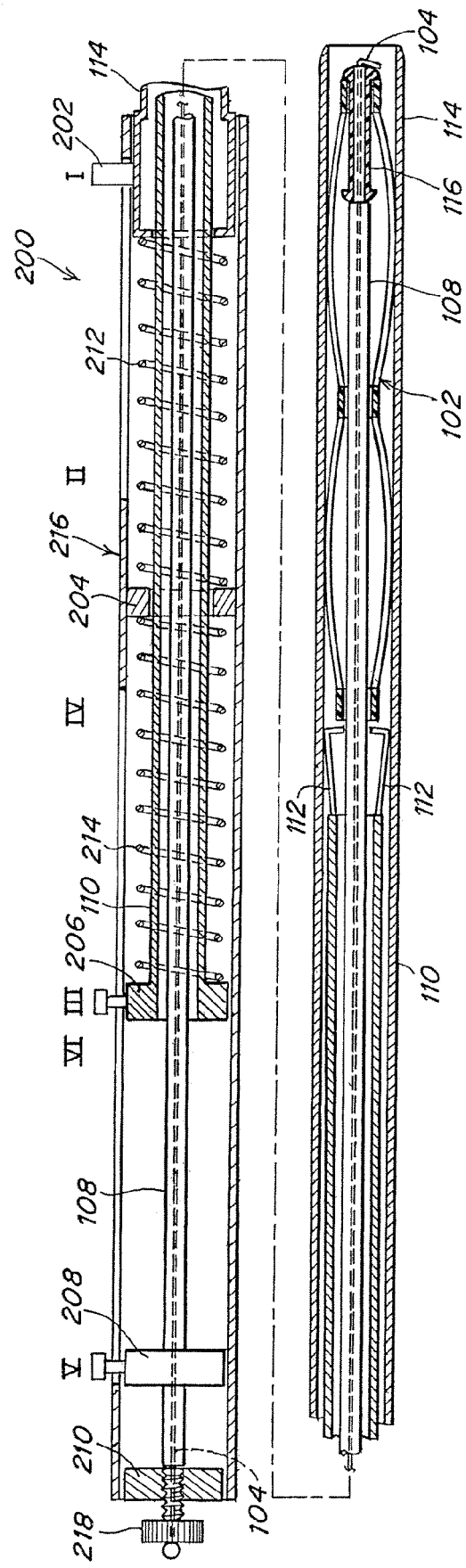
FIG. 20 shows a handle for use with the occluder delivery/recovery system of FIG. 2.

FIG. 20 shows a handle 200 for use with the occluder delivery/recovery system 100 described herein. The general procedure for inserting and/or removing an implant is similar to that described in connection with FIGS. 3-14, above. The handle 200 includes a delivery knob 202 attached to the sheath 114, and operates between two primary positions, as further described herein. A separator 204 separates recovery and delivery springs, and provides a small amount of compression to the springs in their most extended configuration. A recovery knob 206 attaches to the recovery catheter 110 and operates between two primary positions as further described herein. A mandrel knob 208 attaches to the mandrel 108 and operates between two primary positions, as further described herein. A delivery wire knob 210 attaches to the delivery wire 104 and the mandrel 108. A delivery spring 212 compresses between the delivery knob 202 and the separator 204, so that withdrawal of the delivery knob 202 away from the occluder 202 compresses the delivery spring 212. A recovery spring 214 is disposed between the recovery knob 206 and the separator 204, so that advancing the recovery knob 206 toward the occluder 102 compresses the recovery spring 214.

A handle housing 216 provides a casing for the other handle components and restricts their movements to within predetermined ranges. The casing may have an ergonomic design so that the various components are easily accessible to the operator, and the required manipulations can be performed in an efficient and repeatable manner.

A detachment screw 218 mates with the delivery wire knob 210, and is fixedly attached to the delivery wire 104. Rotating the detachment screw 218 incrementally pulls on the delivery wire 104 with significant force, but in a controlled manner, pulling the bend in the distal end of the delivery wire 104 against the mandrel tip 106, thereby straightening the bend and releasing the implant from the delivery/recovery system 100.

Figure 21:
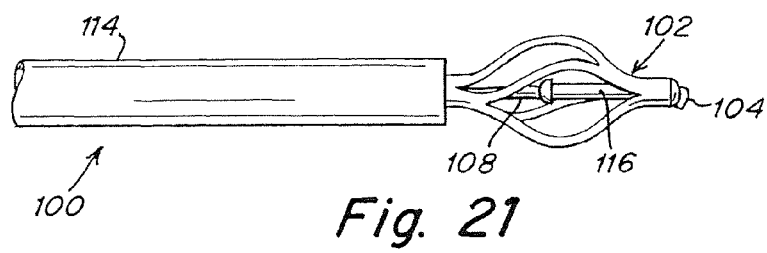
FIGS. 21 through 25 show stages of a delivery sequence using the handle of FIG. 20; and, FIGS. 26 through 30 show stages of a recovery sequence using the handle of FIG. 20.
Figure 22:
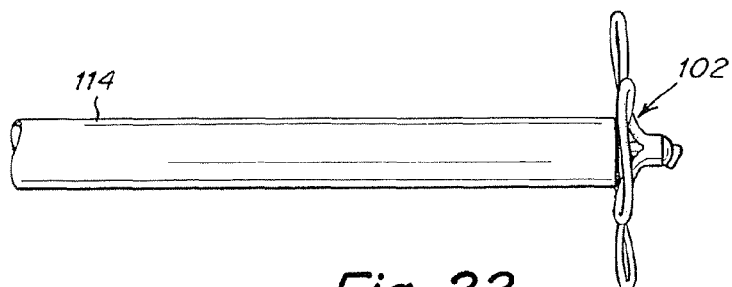

The delivery sequence for deploying an occluder 102 using the handle 200 begins with the distal end of the delivery/recovery system 100 inserted through the PFO tunnel 18 from the right atrial side and extended partially into the left atrium 13. As used herein, the term "retract" means to pull away, longitudinally, from the distal end of the delivery/recovery system 100. The term "advance" means to push, longitudinally, toward the distal end of the delivery/recovery system 100. The operator begins the delivery sequence by retracting the delivery knob 202 from position I to position II, which compresses the delivery spring 212 and uncovers the distal half of the occluder 102, as shown in FIG. 21. This allows the occluder clover petals to relax and partially expand away from the central axis. The operator then releases the delivery knob 202, and the delivery spring 212 forces the delivery knob 202 back to position I. The movement of the sheath 114 presses against the clover petals, causing them to fully expand on the left atrial side of the PFO, as illustrated in FIG. 22.

Figure 23:
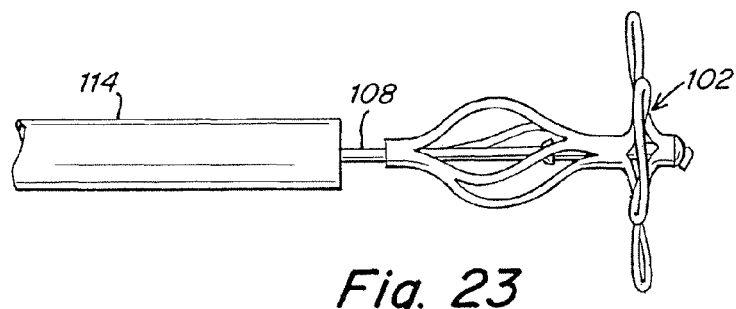
Figure 24:
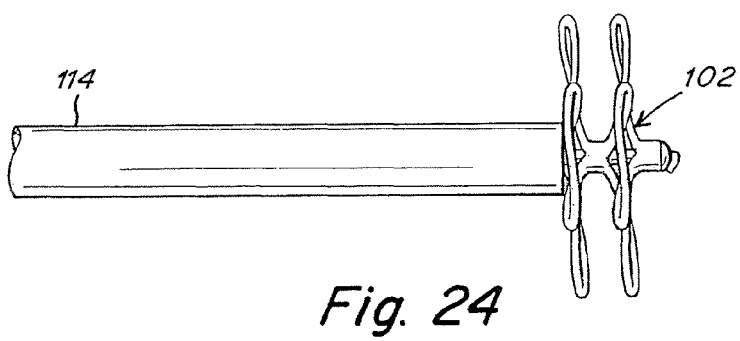
Figure 25:
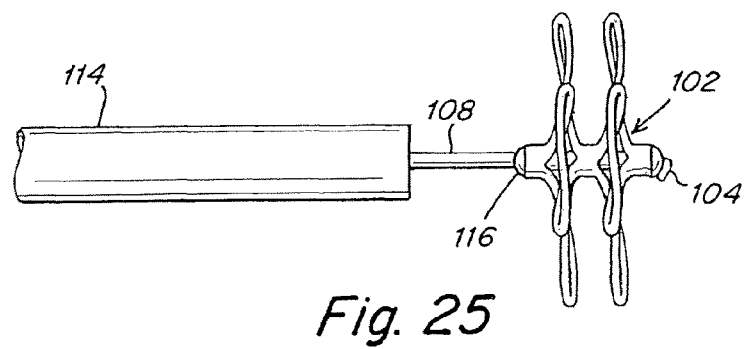

The operator again retracts the delivery knob 202 from position I to position II, uncovering the proximal half of the occluder 102, allowing the proximal petals to expand partially away from the central axis, as shown in FIG. 23. The operator releases the delivery knob 202, the delivery spring 212 forces the delivery knob 202 back to position I, and the sheath 114 presses against the proximal occluder petals causing them to fully expand on the right atrial side of the PFO, as illustrated in FIG. 24. The sheath 114 pressing against the proximal occluder petals forces the proximal end of the occluder 102 over the proximal stop of the catch member 116, thereby locking the occluder 102 in its deployed position. The operator then retracts the delivery knob 202 to position II and locks it into place (using a locking slot, a set screw, or some other similar locking mechanism known in the art). This retracts the sheath 114 away from the occluder 102, as shown in FIG. 25.

If the operator determines that the occluder 102 is in the proper position, the operator removes the bend in the distal end of the delivery wire 104 by turning the detachment screw 218, which pulls the bend against the mandrel tip 106 and forces the bend to straighten. The operator then pulls the mandrel away from the deployed occluder 102 and removes the delivery/recovery system 100 from the patient.

Figure 26:
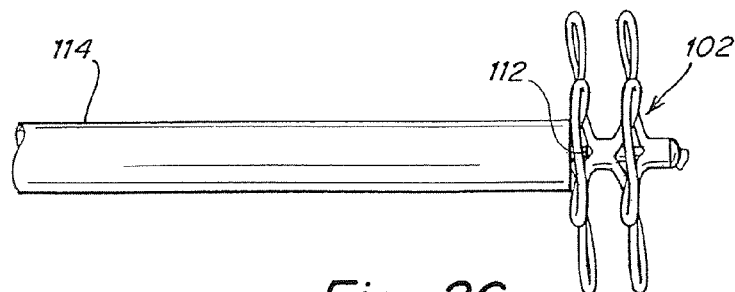
Figure 27:
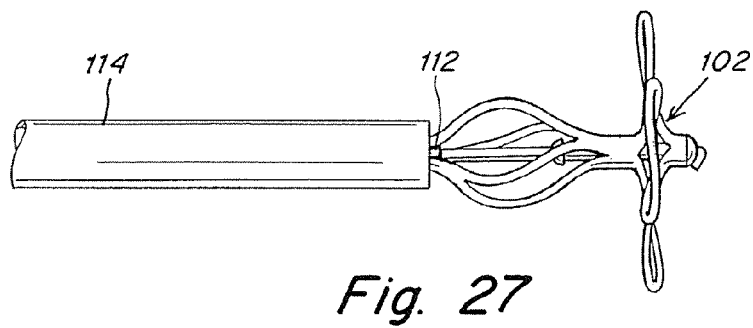
Figure 28:
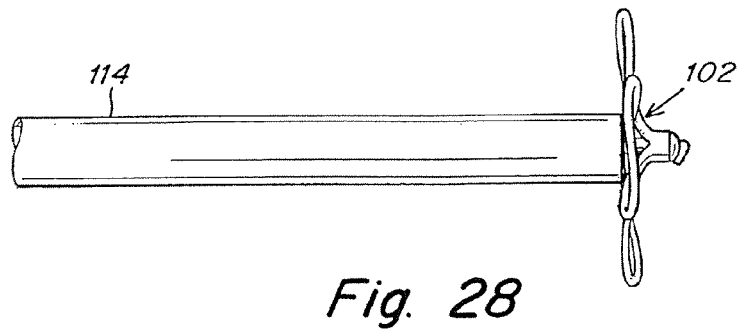
Figure 29:
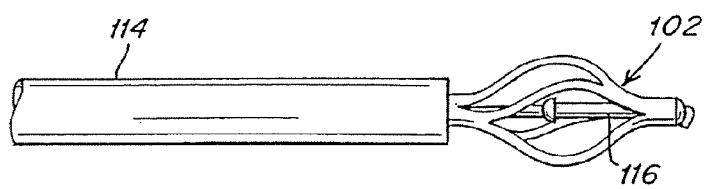
Figure 30:
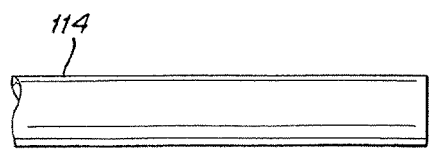

If the operator determines that the occluder 102 is not in the proper deployed position, the operator begins the recovery sequence by advancing the recovery knob 206 from position III to position IV, compressing the recovery spring 214 and advancing the claws 212 outside of the sheath 114 and toward the proximal end of the occluder 102. The operator then releases the delivery knob 202 from the locked position II to position I, which forces the sheath 114 over the claws 112, clamping the claws onto the proximal end of the occluder 102, as shown in FIG. 26. The operator then advances the mandrel knob 208 from position V to position VI, causing the mandrel 108 to push the proximal stop of the locking member 116 through the proximal end of the occluder 102, unclamping the proximal part of the occluder 102 and allowing the proximal clover petals to elongate, as shown in FIG. 27. Note that once the occluder 102 is unclamped, the spring force of the compressed recovery spring 214 pushes the recovery knob 206 from position IV to position III, which causes the claws 112 to pull the proximal half of the occluder 102 into the sheath, along with the mandrel knob 208 from position VI to position V to completely withdraw the proximal petals of the occluder 102 into the sheath 114, as shown in FIG. 28. The operator then advances the mandrel knob 208 from position V to position VI, which allows the distal petals of the occluder 102 to relax and elongate, as shown in FIG. 29. The mandrel knob 208 retracts automatically (via spring force, or in some cases with assistance from the operator) from position VI to position V, withdrawing the occluder completely into the sheath 114, as shown in FIG. 30. The sheath may be left behind to allow for another delivery. The operator may remove the recovered occluder 112 and the delivery/recovery system 100 from the patient, or redeploy it.

The delivery system can be used with other embodiments that have internal interference catching systems. These systems typically include components that pass through a center joint of an implant along a longitudinal axis. This type of catch member typically has a section or sections with a larger outside diameter (OD) than the inside diameter (ID) of the implant, so the catch member can engage the implant in one of several ways, such as: (a) the section of the catch member with a larger OD compresses during the catching process as the catch member passes through the implant, and/or (b) the implant ID increases during the catching process as the catch member passes through the implant. In either case, a proximal tip of the catch member passes through the implant device, the dimensions of both the device and the implant return to more or less their original state, thereby holding the implant. Another option is that the catch member or part of the implant can deform temporarily to allow the catching member to pass through.

Figure 31A:
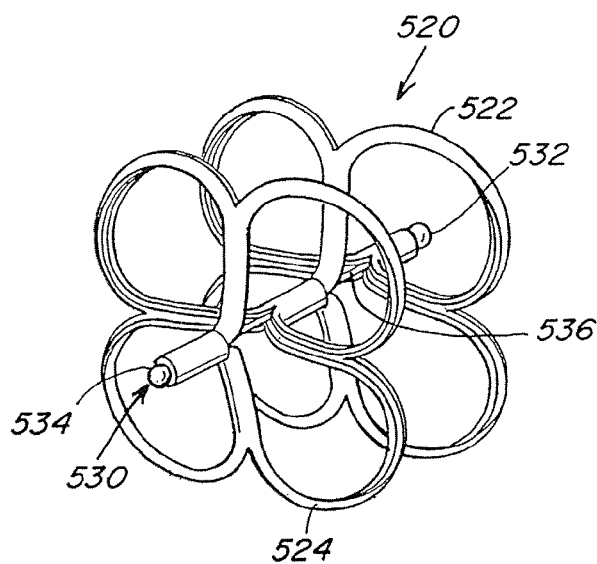
FIGS. 31a and 31b show another embodiment of an occluder that may be used with some of the delivery systems herein.

FIG. 31a illustrates another embodiment of a septal occluder that may be delivered using a system of the type described herein. In this case, an occluder 520 in a deployed position has a distal (left atrial) side 522 and a proximal side 524, each with four petals. A catch mechanism 530 has a distal ball 532, a proximal ball 534, and a rod 536 connecting balls 532 and 534. Balls 532, 534 and rod 536 can each have a central bore (not shown) to allow catch mechanism 530 to be delivered with occluder 520 over a guide wire, and can allow a bent wire to pass through as in FIGS. 2 and 3. Other types of occluders, for example, those with petals having solid or mesh surfaces, or those with tissue scaffolds may also be used.

Figure 31B:
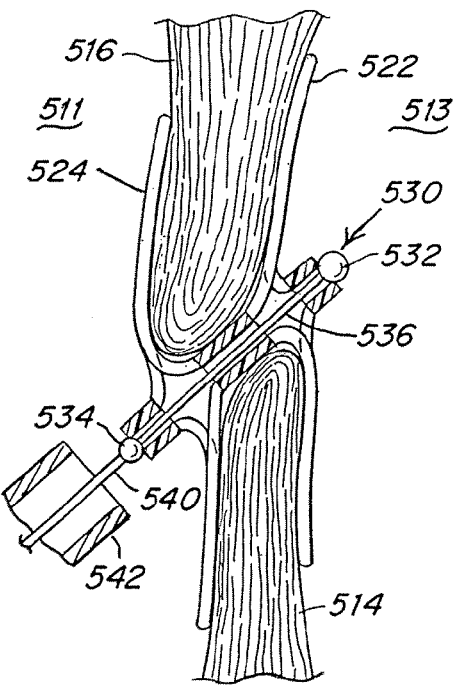

FIG. 31b is a side view showing occluder 520 with left atrial side 522 and a right atrial side 524, each in contact with septum secundum 516 and septum primum 514. In this figure, the catch mechanism is shown with a delivery wire 540 and sheath 542 in a connected position before the delivery wire 540 would be detached from ball 534.

As described in the incorporated application Ser. No. 10/890,784, a device of this type can be formed by making cuts or slits in a tube and compressing the ends. The tube can be made of a polymer. In this embodiment and others, the device can be made of a polymer that can be bioresorbable or not bioresorbable.

Figure 34:
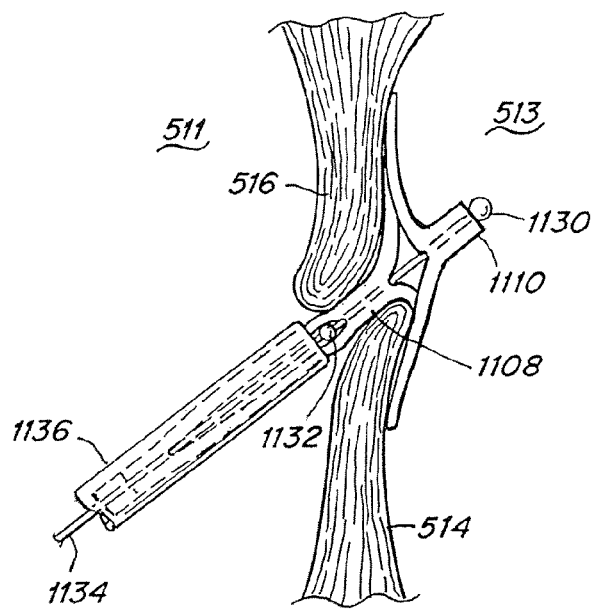
Figure 35:
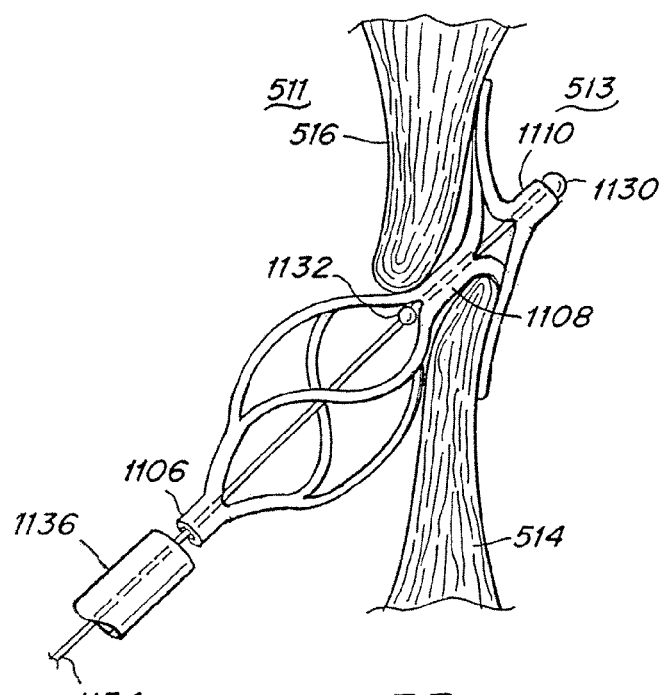
Figure 36:
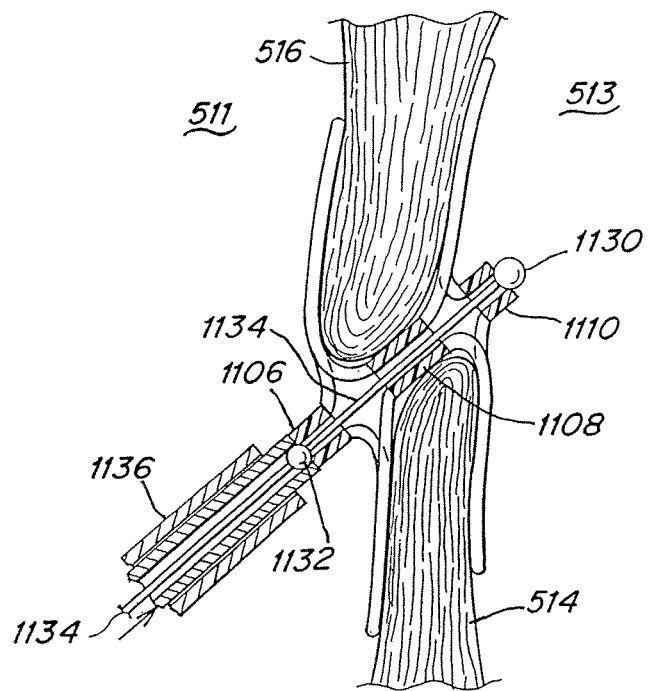

FIG. 32 shows an occluder with a ball and string for catching and holding a device mechanism. In the extended configuration for delivery (shown in FIG. 32 within a delivery sheath 1136), the distal ball 1130 engages the distal joint 1110, and the proximal ball 1132 is disposed along the delivery string 1134 between the distal joint 1110 and the center joint 1108. FIGS. 33 through 36 show the delivery sequence for the ball and string mechanism of FIG. 32. A shown in FIG. 33, the distal portion of the occluder is deployed from the delivery sheath 1136 on the left atrial side of the PFO. FIG. 34 shows the proximal ball 1132 pulled through the center joint 1108, thereby locking the distal portion of the occluder. FIG. 35 shows the proximal portion of the occluder deployed from the delivery sheath 1136 on the right atrial side of the PFO. FIG. 36 shows the proximal ball 1132 pulled through the proximal joint 1106, thereby locking the proximal portion of the occluder. Detaching wire 1134 from ball 1132 is the step remaining to complete the delivery of the occluder in the PFO.

Figure 37:
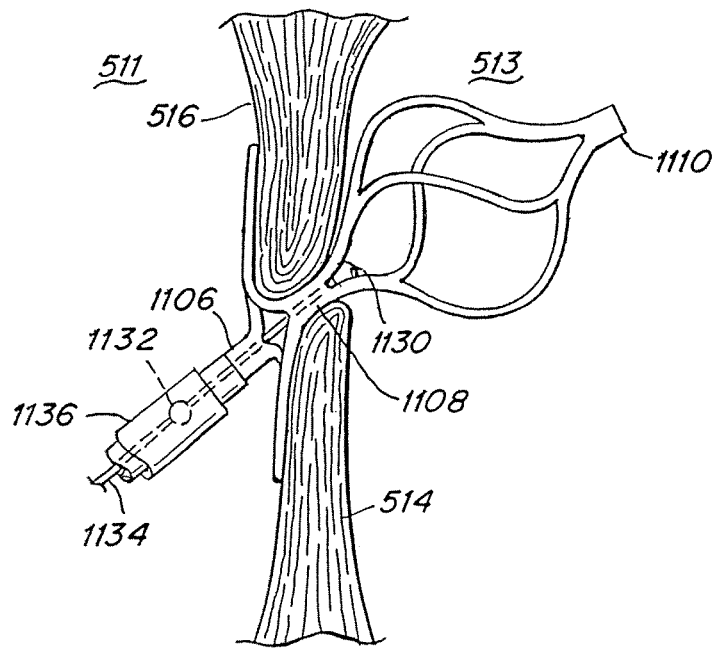
Figure 38:
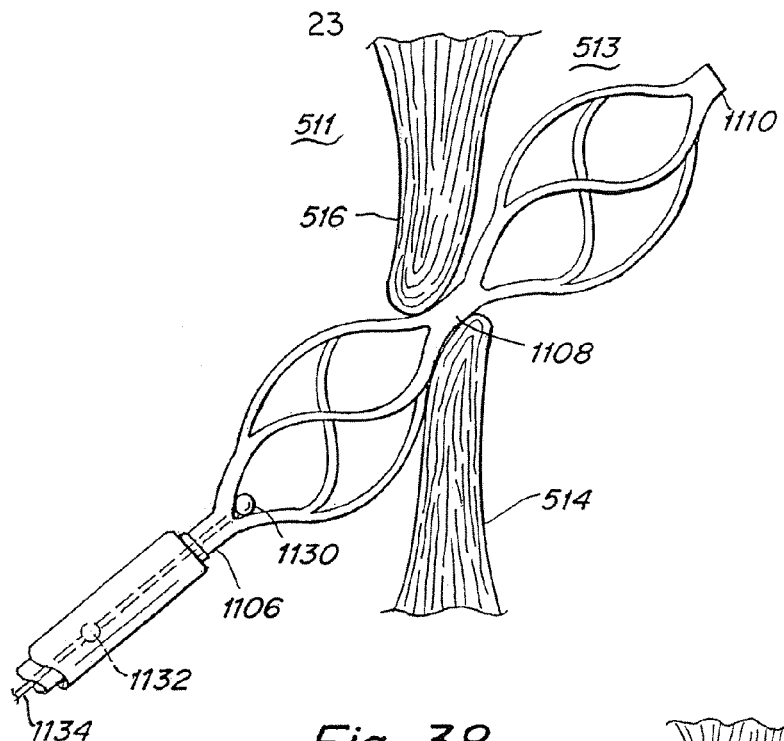
Figure 39:
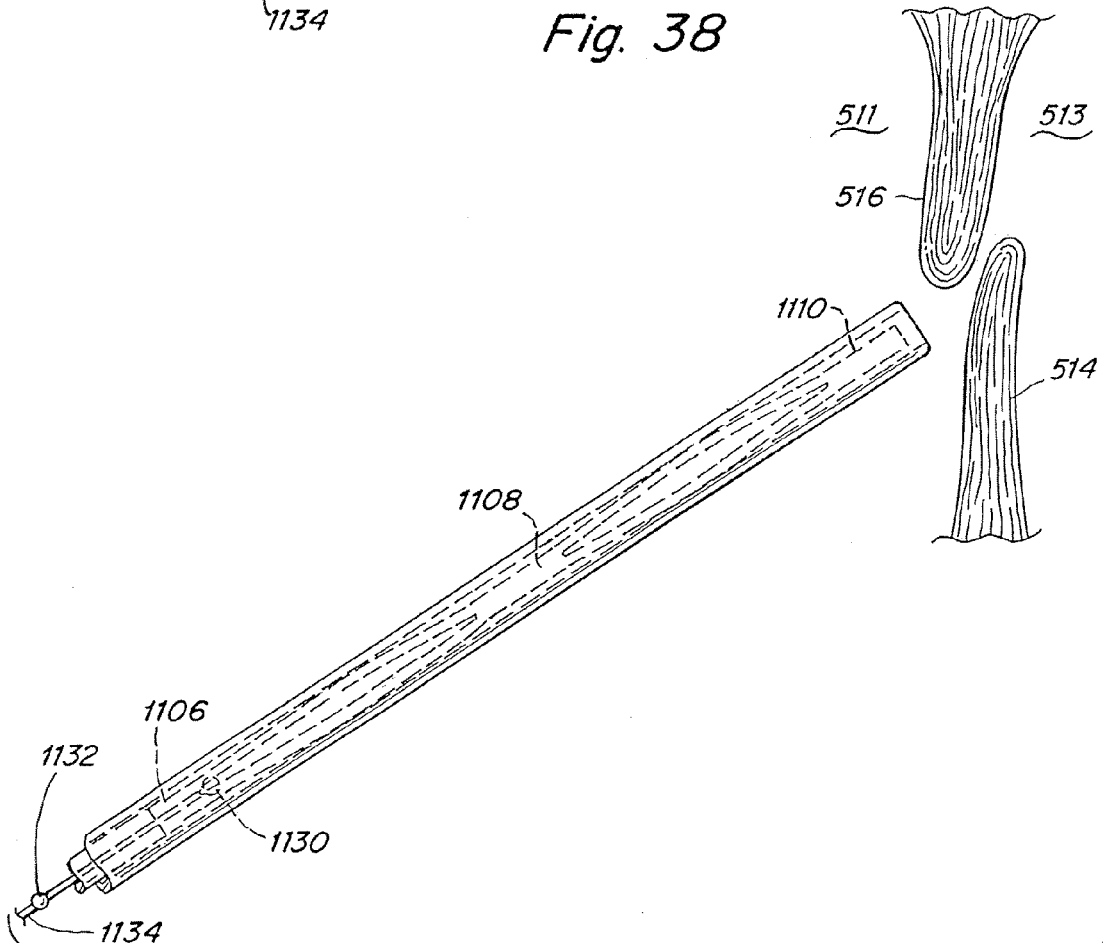

FIGS. 37 through 39 show a recovery sequence for removing an occluder, such as that delivered in the manner shown in FIGS. 33 through 36. FIG. 37 shows the delivery sheath 1136 disposed against the proximal end of the occluder. Wire 1134 has been pulled with sufficient force to pull ball 1130 through the distal joint 1110 thereby allowing the distal side of the occluder to start to return toward a tubular shape. FIG. 38 shows the distal ball 1130 further pulled through the center joint 1108, and up against the proximal joint 1106, so the right atrial side starts to lose its compressive force. FIG. 39 shows the unlocked occluder after it has been retracted back into the delivery sheath and out of the PFO by advancing the sheath, retracting the device, or some combination of these motions. Another method for recovering the device is using a method similar to that shown in a provisional application entitled "Closure Device With Hinges", provisional application No. 60/569,203, filed May 7, 2004, which is incorporated herein by reference. In that method, a set of claws is used to grip and pull the device, starting with the proximal joint.

In the embodiment of FIGS. 32-39 and in other embodiments, the balls need not be preferably spherical, but could be altered, such as having a distal ball with a flattened distal end. As with the delivery system of FIG. 2, the balls can have bores, and a bent wire or other mechanism can prevent the occluder from moving in a distal direction when it is desirable to prevent such movement.

The following embodiments include "two elements" catching systems. The two elements systems operate on the principle that two elements work together such that either one is small enough to pass through an occluder center joint, but the two elements together form a unit that is too big to pass through an occluder center joint.

Figure 40:
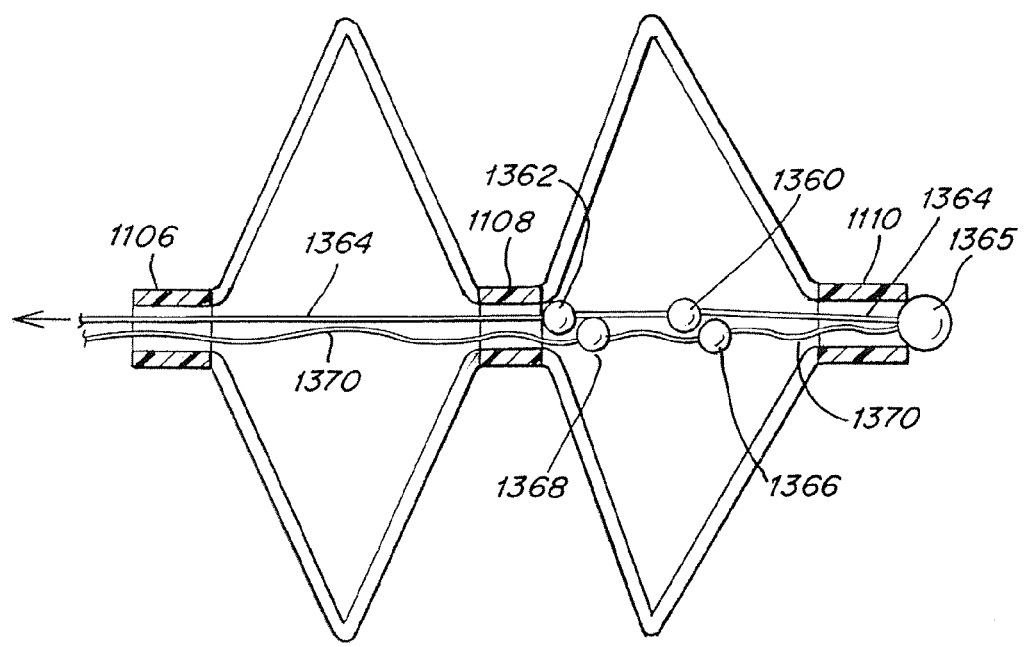
FIGS. 40 through 45 show several further embodiments of occluders.
Figure 41:
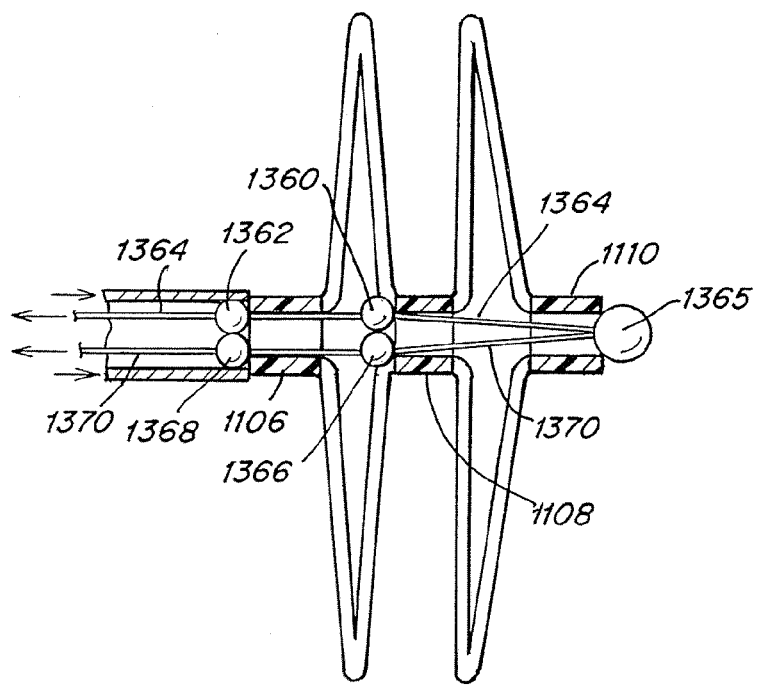

FIGS. 40 and 41 show one type of two elements catching system, including multiple pairs of balls distributed along a pair of strings. In FIG. 40, a first ball 1360 and a second ball 1362 are fixedly attached to a first string 1364 (or wire or suture). The distal end of the first string 1364 is releasably attached to a ball 1365 that is part of the distal joint 1110, either held to the distal end by the tension, or fixedly connected to the distal end. The proximal end of the first string 1364 extends out through a center joint 1108 and a proximal joint 1106 to the operator. A third ball 1366 and a fourth ball 1368 are fixedly attached to a second string 1370. The distal end of the second string 1370 is releasably attached to the ball 1365 at the distal joint 1110, and the proximal end of the second string 1370 extends out through the center joint 1108 and the proximal joint 1106 to the operator. The length of the first string 1364 from the first ball 1360 to the distal joint is the same as the length of the second string 1370 from the third ball 1366 to the distal joint 1110. The length of the first string between the first ball 1360 and the second ball 1362 is the same as the length of the second string 1370 from the third ball 1366 to the fourth ball 1368. These lengths ensure that the first ball 1360 and third ball 1366 will be side by side (i.e., at the same point) along the longitudinal axis of the occluder, and the second ball 1362 and the fourth ball 1368 will be side by side along the longitudinal axis of the occluder. At least one of the strings can be elastic, in this case string 1364, so that one of the strings may be stretched to stagger the balls along the longitudinal axis, as shown in FIG. 40. Each of the strings 1364 and 1370 can include multiple string segments. In each case, the strings can be fixedly connected to the respective balls if a mechanism is provided to cut the strings after delivery.

To deploy the occluder, the operator pulls one of the strings in a proximal direction to stagger the first and third balls, and the second and fourth balls. While the balls are staggered, the operator pulls both strings until the first ball 1360 and the third ball 1366 are on the proximal side of the center joint 1108, and the second ball 1362 and the fourth ball 1368 are on the proximal side of the proximal joint 1106. The operator then releases the string that is in elastic tension, so as to return the first/third and the second/fourth ball pairs in the side-by-side configuration. When the first/third ball and the second/fourth pairs are in side-by-side configuration, as shown in FIG. 41, the pairs cannot pass through the center joints, thereby locking the occluder. The strings are then detached or cut from the device to complete delivery.

To unlock the occluder before the delivery strings are detached, the operator pulls on one of the strings to once again stagger the balls, thereby allowing the staggered balls to pass through the center joints.

Other embodiments may stagger the balls via other techniques. For example, the first string 1364 and second string 1370 may be one continuous string that passes through the distal joint and can slide along a fixed or rotatable axle, so that the distal joint 1110 acts as a pulley. The operator pulls on one of the strings to stagger or realign the ball pairs.

Figure 42:
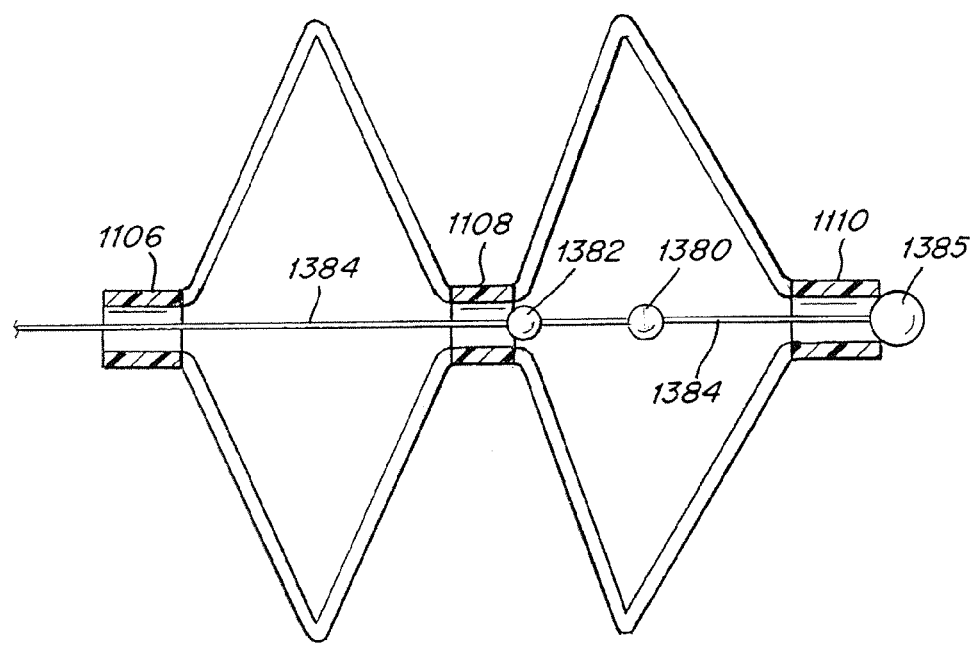
Figure 43:
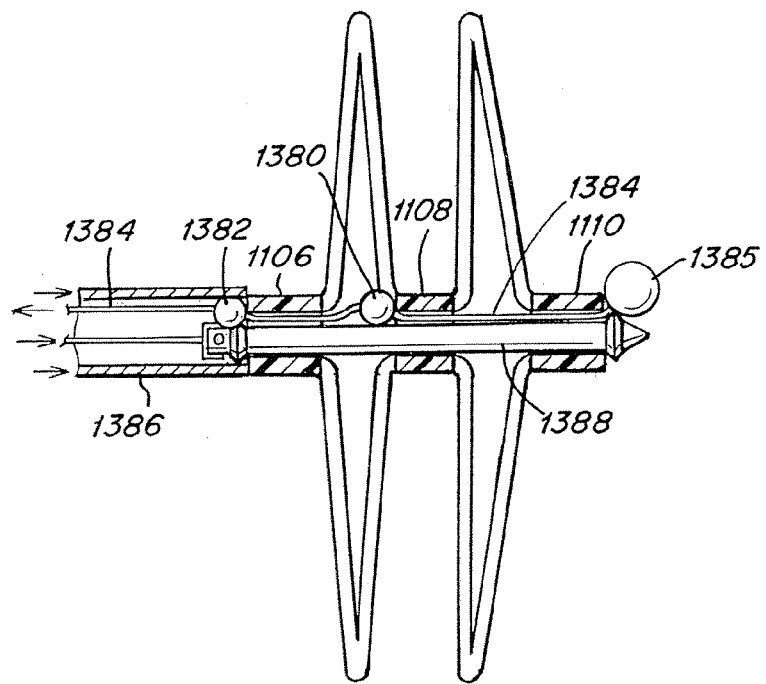

FIGS. 42 and 43 show yet another two element catching system for an occluder. A first ball 1380 and a second ball 1382 are fixedly attached to a string 1384 (or wire, suture, or tube). The distal end of the string 1384 is fixedly attached to a ball 1385 that forms part of the distal joint 1110, and the proximal end of the string 1384 passes through the center joint 1108 and the proximal joint 1106 and out to the operator. To deploy the occluder, the operator pulls the string 1384 until the occluder stops against a delivery sheath 1386. The operator continues to pull the string 1384 until the first ball 1380 is on the proximal side of the center joint 1108 and the second ball 1382 is on the proximal side of the proximal joint 1106. The operator then inserts a rod 1388 through the proximal joint 1106, the center joint 1108, and the distal joint 1110, as shown in FIG. 43. The outside diameter of the rod 1388 is large enough to prevent either ball from passing through a center joint while the rod 1388 is disposed within the center joints as shown in FIG. 43. Note that the string 1384 may include multiple string segments. The method of using claws, as referred to in conjunction with FIGS. 37-39, could also be used here to recover the device.

Figure 44:
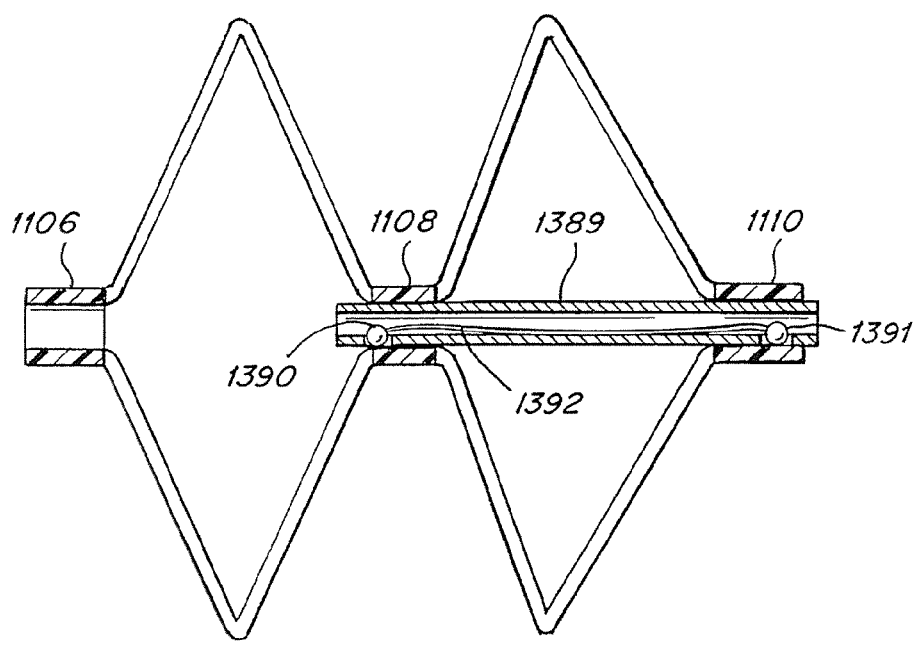
Figure 45:
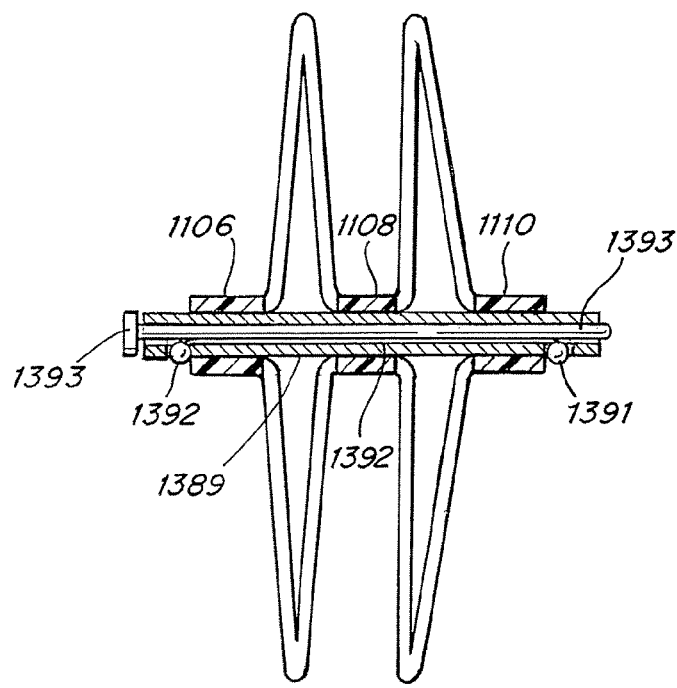

FIGS. 44 and 45 illustrate another embodiment similar to that shown in FIGS. 42 and 43. A tube 1389 with an outside diameter slightly smaller than the inside diameter of the center joints includes two apertures in the side wall, each large enough for a first ball 1390 or a second ball 1391 to pass. A string 1392 attaches the first ball 1390 to the second ball 1392. The operator deploys the occluder within the PFO by moving the distal joint 1110 toward the proximal joint 1106, using any one of several delivery techniques described herein or known in the art. The operator then inserts the rod 1393, thereby retaining each ball in its respective aperture. At least a portion of each ball extend beyond the outside diameter of the locking tube 1389 in this position, preventing the proximal joint 1106 from moving in the proximal direction or the distal joint from moving in the distal direction, thereby locking the occluder.

Figure 46:
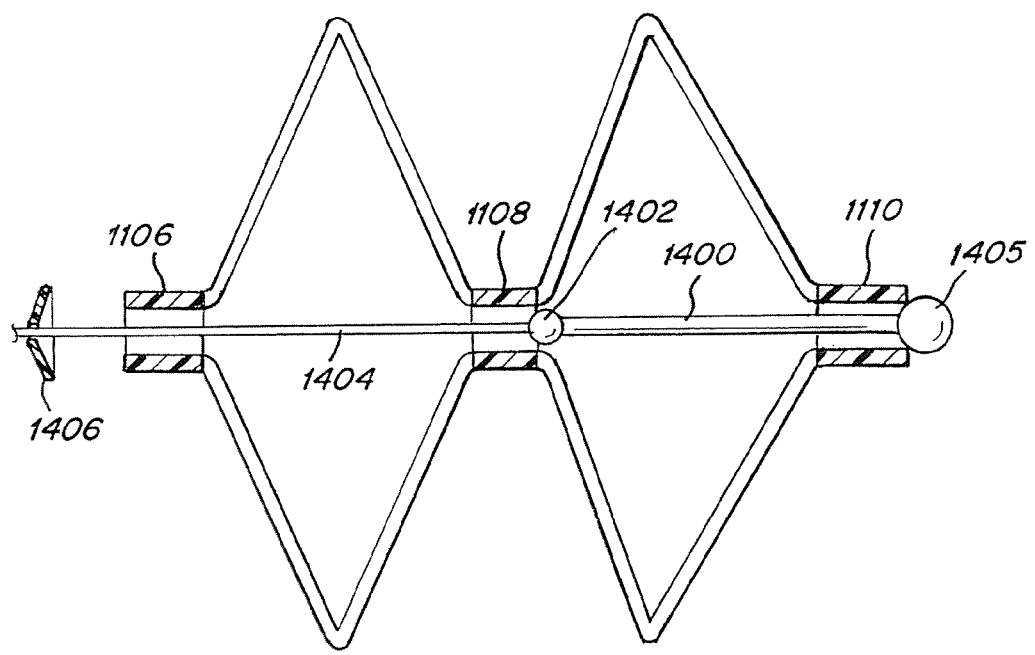
FIGS. 46 through 48 show still further embodiments of occluders, these with an end cap lock stop.
Figure 47:
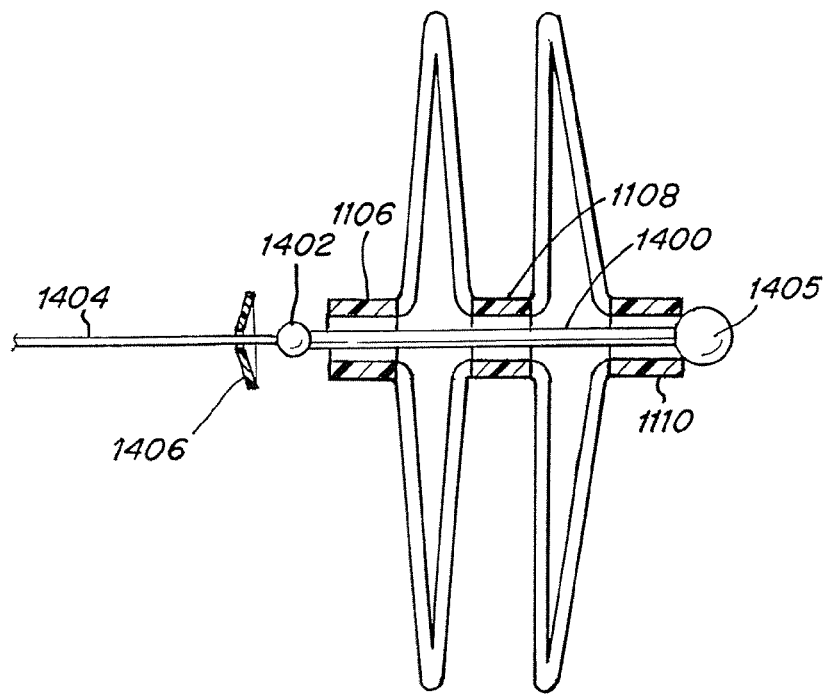
Figure 48:
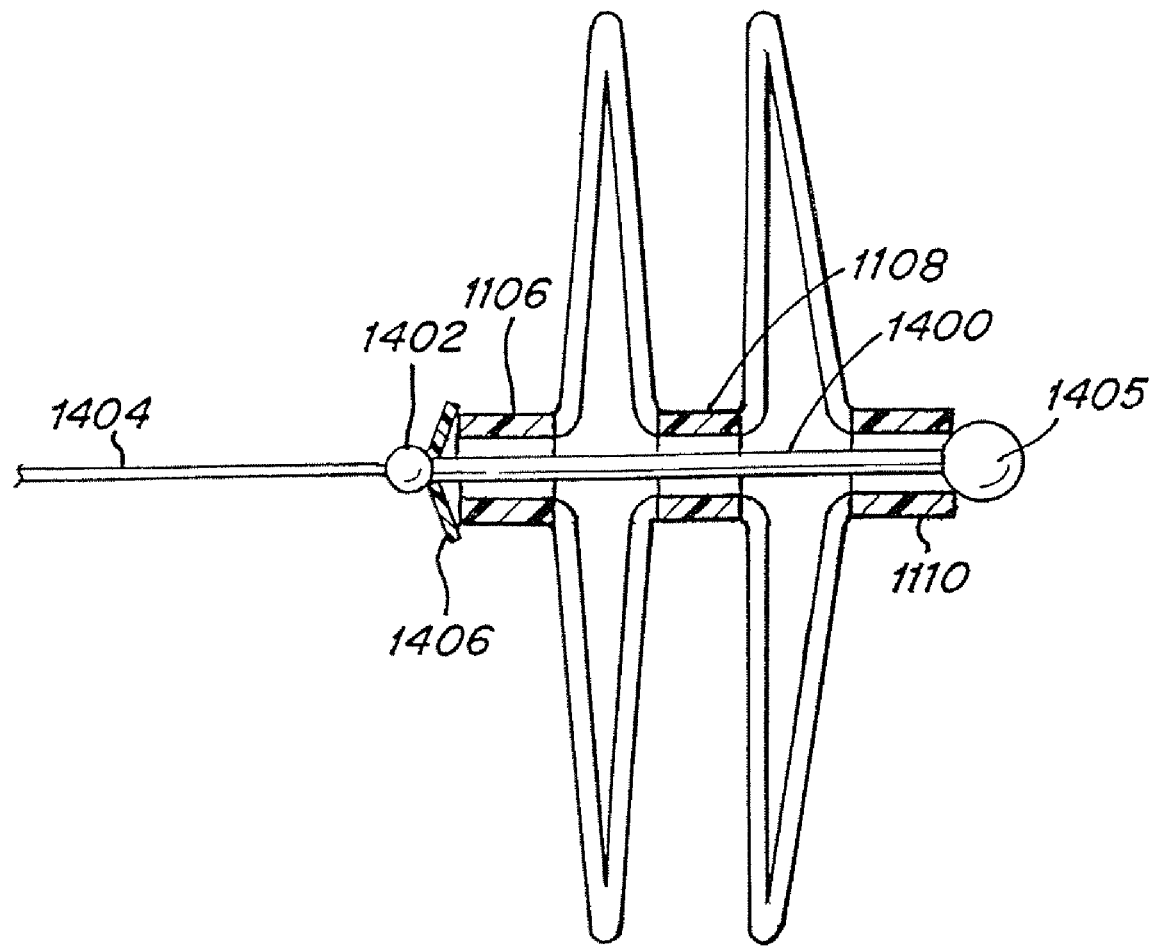

FIGS. 46-48 show an embodiment of an end cap catching mechanism, including a catch member 1400 with a proximal ball 1402 fixedly attached to its proximal end, and its distal end fixedly attached to the distal joint 1110. This embodiment shows the distal end of the catch member 1400 fixedly attached to a ball 1405 having an outside diameter larger than the inside diameter of the distal joint 1110, although other techniques of securing the distal end of the catch member 1400 to the distal joint may also be used. The outside diameter of the proximal ball 1402 may be slightly less than the inside diameter of the center joint 1108 and the proximal joint 1106. A detachable delivery wire 1404 (or delivery shaft) attaches to the proximal ball 1402, and a cap 1406 is disposed about the delivery wire 1404 on the proximal side of the locking ball 1402.

The operator engages this catch mechanism by pulling on the delivery wire 1404 so as to pull the distal joint 1110 in a proximal direction toward the proximal joint 1106. Once the proximal ball 1402 is on the proximal side of the proximal joint 1106, as shown in FIG. 47, the operator pushes the cap 1406 over the ball 1402. In order to pass through the cap 1406 in the proximal direction, the ball 1402 deforms cap 1406, expanding the inside diameter of the cap 1406. Once the ball 1402 is through the cap locking 1406, the cap 1406 returns to its original shape, resisting the ball 1402 from passing back through the cap 1406 in a distal direction. The delivery wire 1404 is then detached from ball 1402 if releasably attached to it, or is cut to sever the connection to ball 1402.

In one embodiment, the cap has threads on its distal side, so that the cap 1406 can be screwed onto mating threads disposed on the outside of the proximal portion of the proximal joint 1106. In other embodiments, a claw can be used to grip the ball 1402.

Having described several embodiments, it should be apparent that modification can be made and be within the scope of the appended claims. For example, other shapes and materials can be used.

What is claimed is:

1. A method for operating a delivery system for delivering a septal occluder device in a delivery sheath to a living body, the device adapted to be elongated along an axial direction when in the sheath in a delivery position, the device including one or more expanding portions that expand in a radial direction perpendicular to the axial direction when delivered to form a deployed configuration, the device further including a catch mechanism for holding the device in the deployed position when in the living body, wherein the delivery system comprising:
  a mandrel extending along the axial direction and through at least a portion of the device while the device is in the delivery position, wherein the mandrel contacts the catch mechanism at a proximal end of the catch mechanism, and limits movement by the catch mechanism in the proximal direction;
  a wire extending along the axial direction and through the mandrel and the device, the wire including a distal end that extends beyond a distal end of the device and that is adapted for limiting movement by the device in the distal direction, the wire being removable while the mandrel is still in contact with the catch mechanism;
  a sheath for enveloping the wire, the mandrel, and the device; and
  wherein the sheath, mandrel, and wire being movable relative to each other and to the device in a series of steps for allowing the expanded portions of the device to expand, and for the catch mechanism to hold the device in its expanded configuration; and
the septal occulder device comprising a center joint for passing through a defect, a distal expandable component for expanding on a distal side of the defect, a proximal expandable portion for expanding on a proximal side of the defect, and a catch mechanism that includes a first stop at a distal end of the catch mechanism, and a second stop at a proximal end of the catch mechanism;
the method comprising:
  providing the sheath into the distal side of the defect and withdrawing the sheath while limiting the device from moving in the proximal direction to allow the distal expandable component to expand on the distal side of the defect;
  moving the center joint relative to the catch mechanism to cause the second stop to pass through the center joint;
  further withdrawing the sheath while limiting the device from moving in the proximal direction to allow the proximal expandable component to expand on the proximal side of the defect; and
  moving the proximal end of the device relative to the catch mechanism to cause the second stop to pass through the proximal end.

2. The method of claim 1, further comprising removing the sheath, mandrel, and wire from the body and leaving the device in the body.

3. The method of claim 2, wherein the wire has a bent end for limiting proximal movement by the catch mechanism, wherein removing the wire includes moving one of the mandrel and the wire relative to the other to straighten the bent portion.

4. The method of 1, further including grasping the device at the proximal end and pulling to cause the proximal expanded component to return to the delivered configuration while limiting movement of the catch mechanism in the proximal direction.

5. The method of claim 4, further comprising moving the proximal end of the catch mechanism in a distal direction relative the center joint to cause the proximal end to pass through the center joint and to allow the distal expandable component to return to its delivered position.

6. The method of claim 1, wherein the catch mechanism further includes a third stop between the distal and proximal stops, the method including moving the center joint relative to the third stop to cause the center joint and the distal end to be clamped between the first and third stops.

7. The method of claim 1, wherein the method includes delivering a PFO occluder that has on each side of the defect one of loops, open ended struts, or struts that double back from the center joint to an end of the occluder.

8. The method of claim 1, wherein delivery system further includes springs for biasing the catheter and mandrel, the providing and withdrawing steps are performed by controlling positions of the springs.

9. A delivery system for delivering a medical device in a delivery sheath to a living body, the device adapted to be elongated along an axial direction when in the sheath in a delivery position, the device including one or more expanding portions that expand in a radial direction perpendicular to the axial direction when delivered to form a deployed configuration, the device further including a catch mechanism for holding the device in the deployed position when in the living body, the system comprising:
  a catheter extending along the axial direction, the catheter including claws, the claws being disposed at a distal end of the catheter and including grasping elements biased away from a central axis of the catheter, the grasping elements capable of movement toward the central axis of the catheter for grasping the device when partially deployed and for withdrawing the device back into a sheath for repositioning and/or removal from the body;
  a mandrel extending along the axial direction and through the catheter and at least a portion of the device and for contacting the catch mechanism at a proximal end of the catch mechanism for limiting movement by the catch mechanism in the proximal direction;
  a wire extending along the axial direction and through the catheter, the mandrel, and the device, the wire including a distal end that extends beyond a distal end of the device and that is adapted for limiting movement by the device in the distal direction, the wire being removable while the mandrel is still in contact with the catch mechanism; and
  the sheath for enveloping the wire, the mandrel, the catheter, and the device;
  the sheath, catheter, mandrel, and wire being movable relative to each other and to the device in a series of steps for allowing the expanded portions of the device to expand, and for the catch mechanism to hold the device in its expanded configuration.

10. A method for operating the delivery system of claim 9 with a septal occluder device that has a center joint for passing through a defect, a distal expandable component for expanding on a distal side of the defect, a proximal expandable portion for expanding on a proximal side of the defect, and a catch mechanism that includes a first stop at a distal end of the catch mechanism, and a second stop at a proximal end of the catch mechanism, the method comprising:
  providing the sheath into the distal side of the defect and withdrawing the sheath while limiting the device from moving in the proximal direction to allow the distal expandable component to expand on the distal side of the defect;
  moving the center joint relative to the catch mechanism to cause the second stop to pass through the center joint;
  further withdrawing the sheath while limiting the device from moving in the proximal direction to allow the proximal expandable component to expand on the proximal side of the defect; and
  moving the proximal end of the device relative to the catch mechanism to cause the second stop to pass through the proximal end.

11. The method of claim 10, wherein the catch mechanism further includes a third stop between the distal and proximal stops, the method including moving the center joint relative to the third stop to cause the center joint and the distal end to be clamped between the first and third stops.

12. The method of claim 10, wherein the method includes delivering a PFO occluder that has on each side of the defect one of loops, open ended struts, or struts that double back from the center joint to an end of the occluder.

13. The method of claim 10, wherein the wire has a bent end for limiting proximal movement by the catch mechanism, wherein removing the wire includes moving one of the mandrel and the wire relative to the other to straighten the bent portion.

14. A method for delivering an occluder to a defect, the method comprising:
  providing a sheath containing an occluder through a defect and into a distal side of the defect;
  withdrawing the sheath in a proximal direction while limiting the occluder from moving in the proximal direction to extend a distal expandable component of the occluder from a distal end of the sheath to allow the distal expandable component to expand on the distal side of the defect;
  moving a center joint of the occluder and a catch mechanism of the occluder relative to each other to cause a proximal stop disposed on a proximal end of the catch mechanism to pass through the center joint of the occluder;
  further withdrawing the sheath while limiting the occluder from moving in the proximal direction to extend a proximal expandable component of the occluder from the distal end of the sheath to allow the proximal expandable component to expand on a proximal side of the defect; and
  moving a proximal end of the occluder and the catch mechanism relative to each other to cause the proximal stop to pass through the proximal end of the occluder.

15. The method of claim 14, further comprising providing the occluder, the occluder having the center joint for passing through the defect, the distal expandable component for expanding on the distal side of the defect, the proximal expandable portion for expanding on the proximal side of the defect, and the catch mechanism, the catch mechanism including a distal stop at the distal end of the catch mechanism, and the proximal stop at the proximal end of the catch mechanism.

* * * * *